US008142380B2

(12) United States Patent
Hasegawa

(10) Patent No.: US 8,142,380 B2
(45) Date of Patent: Mar. 27, 2012

(54) FOLDING CERVICAL VERTEBRA PROTECTIVE BAND

(75) Inventor: Teiichi Hasegawa, Chiba (JP)

(73) Assignee: Hasegawa Corporation, Yachiyo-Shi (JP)

( * ) Notice: Subject to any disclaimer, the term of this patent is extended or adjusted under 35 U.S.C. 154(b) by 498 days.

(21) Appl. No.: 12/307,712

(22) PCT Filed: Jul. 6, 2007

(86) PCT No.: PCT/JP2007/063571
§ 371 (c)(1),
(2), (4) Date: Jan. 6, 2009

(87) PCT Pub. No.: WO2008/004661
PCT Pub. Date: Jan. 10, 2008

(65) Prior Publication Data
US 2009/0299242 A1 Dec. 3, 2009

(30) Foreign Application Priority Data

Jul. 7, 2006 (JP) ................................. 2006-187474
Nov. 16, 2006 (JP) ................................. 2006-309852
Feb. 6, 2007 (JP) ................................. 2007-026696

(51) Int. Cl.
*A61F 5/00* (2006.01)
*A61F 5/37* (2006.01)
(52) U.S. Cl. ......................................... 602/18; 128/876
(58) Field of Classification Search .................... 602/17, 602/18, 19; 2/468; 128/869, 870, 876; 5/630, 5/636, 637, 640, 643, 622; 606/240
See application file for complete search history.

(56) References Cited

U.S. PATENT DOCUMENTS

| | | | |
|---|---|---|---|
| 3,916,884 A | 11/1975 | Attenburrow | |
| 5,788,658 A * | 8/1998 | Islava | ............................ 602/18 |
| 5,944,016 A * | 8/1999 | Ferko, III | .................... 128/869 |

FOREIGN PATENT DOCUMENTS

| | | |
|---|---|---|
| JP | 44-12702 | 5/1969 |
| JP | 50-63787 A | 5/1975 |
| JP | 61-18893 Y2 | 6/1986 |
| JP | 01-268552 A | 10/1989 |
| JP | 06-12746 Y2 | 1/1994 |
| JP | 06-078943 A | 3/1994 |
| JP | 11-279806 A | 10/1999 |
| JP | 2000-506400 | 5/2000 |
| JP | 2001-025480 A | 1/2001 |
| JP | 2001-523137 A | 11/2001 |
| JP | 2003-019150 A | 1/2003 |
| JP | 2004-305388 A | 11/2004 |
| JP | 2005-027898 A | 2/2005 |

\* cited by examiner

*Primary Examiner* — Patricia Bianco
*Assistant Examiner* — Ophelia Hawthorne
(74) *Attorney, Agent, or Firm* — Birch, Stewart, Kolasch & Birch, LLP

(57) ABSTRACT

A folding cervical vertebra protective band which includes a belt-like protective band body having a length and a width for substantially surrounding an entirety of a cervical portion of a user; and an attachable/detachable fixing means for holding the protective band body, when in use, around the cervical portion, wherein the protective band body has divided components obtained as a result of multiple divisions of the protective band body in a longitudinal direction thereof and also has hinge portions for foldably coupling the multiple divided components to each other when in use and foldably coupling the multiple components together, into a small size when not in use.

21 Claims, 22 Drawing Sheets

(a)

(b)

(a)

(a)

(b)

(c)

(a)

(b)

(c)

(a)

(b)

(a)

(b)

(a)

(b)

(c)

(d)

(a)

(b)

(c)

(a)

(b)

(c)

(d)

(a)

(b)

(a)

(b)

(a)

(b)

(c)

(d)

(a)

(b)

(a)

(b)

(c)

(d)

(a)

(b)

(c)

(d)

(e)

(a)

(b)

(c)

(d)

(a)

(b)

(c) (d) (e)

(a)

(b)

(c)          (d)

(a)

(b)

(c)

(d)

(a)

(b)

(c)    (d)

(a)

(b)

(c)

FOLDING CERVICAL VERTEBRA PROTECTIVE BAND

TECHNICAL FIELD

The present invention relates to a cervical vertebra protector used for a purpose of suppression of a movement of a cervical portion, reduction in load of a head weight to a cervical vertebra, health promotion around the cervical portion, and the like for treatment of cervical disorders such as ossification of posterior longitudinal ligament of the cervical portion of a human body, cervical sprain, cervical fracture, and cervical herniation. In particular, the present invention relates to a folding cervical vertebra protective band which is foldable and provided with portability.

BACKGROUND ART

There have been made many suggestions regarding cervical vertebra protective bands used for the purpose of the treatment of cervical disorders. For example, as a belt-like protective band body having a length and a width for surrounding substantially the entire of the cervical portion of a user, the following are suggested: one capable of adjusting the size of the length and/or the width thereof in accordance with the cervical diameter and/or the cervical height of the user, thereby improving stability and fitness in use (Japanese Utility Model Examined Publication No. Sho 44-12702, Japanese Patent Application Laid-open No. Sho 50-63787, and Japanese Utility Model Examined Publication No. Hei 06-12746); one constituted by a size-adjustable collar member and a cover for covering the collar member, being lightweight, having a stiffness sufficient for supporting the cervical portion, and providing excellent wearing comfort at the cervical portion (Japanese Patent Application Laid-open No. 2001-25480); one constituted by a laminated body in which a core member is formed of a shape-maintaining material (Japanese Patent Application Laid-open No. 2004-305388); and one not only being size-adjustable, but also provided with preferable ventilation (Japanese Patent Application Laid-open No. 2005-27898).

Each of the cervical vertebra protective bands as described above supports the weight of the head of the user so as to relieve the load applied to the cervical portion, thereby protecting the cervical vertebra. Thus, the protective band body thereof is made of a relatively stiff material having flexibility, such as a synthetic resin plate, a synthetic resin foam, foam rubber, or a mesh plate. Further, the cervical vertebra protective band is premised on the constant use by the user during treatment. Therefore, even when the cervical vertebra protective band is size-adjustable, it is a common practice for the user to adjust the size of the cervical vertebra protective band in conformity with the cervical portion of oneself so as to maintain, after the adjustment, the state thereof until the end of the treatment.

However, the user of the cervical vertebra protective band as described above is not limited to a relatively seriously-ill patient who is necessary to constantly wear the cervical vertebra protective band under the supervision of a doctor during treatment. Various examples of the user include a mildly-ill patient, a patient almost recovered and wearing the cervical vertebra protective band only in the case where a load is likely to be applied to the cervical portion, a person not wearing the cervical vertebra protective band on the way to workplace but wearing the same at workplace and home, and a person wearing the cervical vertebra protective band only in the case of driving a vehicle or being seated in a vehicle. It is a common practice for those users to handle the cervical vertebra protective band, that is, to wear the same when necessary and to take off and preserve the same.

Meanwhile, it is a common practice for each of the cervical vertebra protective bands which have been suggested and commercially available to be formed in a belt-like shape so as to attain a developed state in which the protective band body thereof has the length and the width (normally, length: 45 to 60 cm and width: 6 to 10 cm) sufficient for surrounding substantially the entire of the cervical portion of each of the large number of users, or to be formed in a looped shape in advance while having the length and the width sufficient for surrounding substantially the entire of the cervical portion of each of the large number of users. The cervical vertebra protective bands are excessively bulky and inconveniently portable.

Regarding any of those conventional cervical vertebra protective bands, focus is exclusively placed on enhancing the cervical vertebra protective function such as restriction of the movement of the cervical vertebra of a patient under treatment or prevention of direct transmission and application of some action including the weight of the head and an impact to the head to the cervical vertebra of the patient under treatment, and on improving the wearing comfort such that the attachment to the cervical portion for a long period of time is not painful. Meanwhile, no attempt has been made to improve the portability thereof in terms of use condition of the user.

In this context, in order to impart the portability to each of the cervical vertebra protective bands as described above, it is possible to design the protective band body thereof to be easily deformed by imparting a predetermined flexibility thereto such that the protective band body is folded several times into a smaller size or curved so as to exhibit a smaller diameter. However, when the protective band body is imparted with the flexibility so as to be easily deformed, the compressive resistance strength of the protective band body is decreased. When the weight of the head is applied to the cervical portion, for example, in the state of a forward inclined posture, the protective band body is easily deformed in some cases, with the result that the cervical vertebra cannot be sufficiently protected.

Patent Document 1: Japanese Utility Model Examined Publication No. Sho 44-12702
Patent Document 2: Japanese Patent Application Laid-open No. Sho 50-63787,
Patent Document 3: Japanese Utility Model Examined Publication No. Sho 61-18893
Patent Document 4: Japanese Utility Model Examined Publication No. Hei 06-12746
Patent Document 5: Japanese Patent Application Laid-open No. 2001-25480
Patent Document 6: Japanese Patent Application Laid-open No. 2004-305388
Patent Document 7: Japanese Patent Application Laid-open No. 2005-27898

DISCLOSURE OF THE INVENTION

Problem to be Solved by the Invention

Under the circumstances, the inventors of the present invention have completed the present invention as a result of intensive studies on the development of a folding cervical vertebra protective band which not only has a sufficient cervical vertebra protective function, but also can be easily folded into a conveniently portable size, and which can be always carried not only by a relatively seriously-ill patient during treatment under the supervision of a doctor, but also by a mildly-ill patient, a patient almost recovered, a person who wants to wear the cervical vertebra protective band in a preventative view only in the case where an unexpected impact, a load, or the like is likely to be applied to the cervical portion although having a trouble with the cervical portion in the past and being unnecessary to wear the same at present, a person who wants to wear the cervical vertebra protective band for the safety and for the purpose of resting the cervical portion when being seated in an automobile or taking rest although not having any trouble with the cervical portion, or others (hereinafter, sometimes collectively referred to as "mildly-ill patient and others") in a bag, a handbag, a pocket of a suit, or the like when necessary, and which can be attached to the cervical portion when necessary.

Accordingly, an object of the present invention is to provide a folding cervical vertebra protective band which not only has a sufficient cervical vertebra protective function, but also can be easily folded into a conveniently portable size.

Means for Solving the Problem

That is, the present invention provides a folding cervical vertebra protective band including:

a belt-like protective band body which has a length and a width for surrounding substantially an entire of a cervical portion of a user; and an attachable/detachable fixing means for holding the protective band body when in use in a use state in which the protective band body is curved around the cervical portion, in which the protective band body has divided components obtained as a result of multiple divisions of the protective band body in a longitudinal direction thereof and has hinge portions for foldably coupling those multiple divided components to each other therebetween, and is attached to the cervical portion while an entire of the protective band body is curved around the cervical portion when in use, and is folded into a small size with use of the hinge portions except when in use.

In the present invention, the protective band body is formed in a belt-like shape so as to have the length and the width required for surrounding substantially the entire of the cervical portion of the user, has the divided components obtained as a result of the multiple divisions of the protective band body in the longitudinal direction thereof, and has the hinge portions for foldably coupling those multiple divided components to each other therebetween. For example, the protective band body may include a pair of dual-divided components which are obtained as a result of a dual division of the protective band body so as to have substantially the same lateral lengths, or may include triple-divided components which are obtained as a result of a triple division of an entire of the protective band body so as to have substantially the same lengths. Further, the protective band body may include the triple-divided components in which a central one of the triple-divided components includes subdivided components which are obtained as a result of a further dual division of the central one of the triple-divided components so as to have substantially the same lateral lengths. Still further, the protective band body may include multiple-divided components which are obtained as a result of multiple divisions, which are performed four times or more, of the entire of the protective band body so as to have substantially the same lengths. Yet further, the protective band body may include subdivided components which are obtained as a result of further multiple divisions of those divided components.

In this context, the entire of the protective band body may be formed of a single plate member, and hinge portions may be formed at predetermined portions thereon by appropriate means described later, to thereby form the multiple divided components. Alternatively, the protective band body may be formed as a laminated body including multiple main body layers which are separated from each other so as to form the multiple divided components and a hinge layer for coupling the multiple main body layers to each other.

Further, the entire of the protective band body is normally curved around the cervical portion when in use so as to be attached to the cervical portion, and hence it is inevitable that the shape thereof in a developed state except when in use is substantially the same shape as the developed surface of the cervical portion, which varies in accordance with the portion in the cervical portion, at which the start point and/or the end point are located. For example, when the start point and the end point thereof are located right in back of the cervical portion, the protective band body exhibits a substantially symmetrical shape with respect to the portion which is at right in front of the cervical portion and serves as the center, that is, the portion covering the Adam's apple of the cervical portion.

It suffices that the entire of the protective band body formed of the multiple divided components as described above is curved around the cervical portion so as to be attached to the cervical portion, and the material therefor is not particularly limited. However, it is preferable that the protective band body be formed as a laminated body which is formed of plate members made of a synthetic resin, a synthetic resin foam, or rubber having flexibility when being formed into a plate member, or of two or more of those materials selected therefrom, which are appropriately selected in terms of required properties such as compressive resistance strength. In addition, while the thickness thereof varies depending on the material used therefor, the protective band body is formed such that the thickness thereof ranges preferably from 0.5 mm to 10 mm in terms of required properties such as compressive resistance strength and fitting comfort, and in terms of weight saving and the portability, ranges more preferably from 1.0 mm to 5 mm, or still more preferably from 1.0 mm to 4 mm.

Examples of the specific material of the divided components constituting the protective band body include: plastics such as polyethylene, polypropylene, polycarbonate, polyamide, acrylonitrile butadiene styrene (ABS), polyethylene terephthalate (PET), polybutylene terephthalate (PBT), an ethylene vinyl acetate copolymer, an olefin-based thermoplastic elastomer, syndiotactic 1,2-polybutadiene, and polyurethane; deformation-retaining plastics each obtained by stretch processing of a polyethylene-based, polypropylene-based, polystyrene-based, polyamide-based, or polyester-based resin; elastomeric plastics formed of an urethane-based, polyamide-based, polyester-based, styrene-based, polyvinyl chloride-based, fluorine-based, or silicon-based resin; rubbers such as synthetic rubbers and natural rubbers, and plastics thereof; veneers each formed of rubber and foam plate thereof; laminated plates each obtained by laminating plastic plates each other; laminated plates each formed of a plastic plate and a rubber plate; laminated plates each formed of a plastic plate and a foam plate; and laminated plates each formed of combination of a plastic plate, a rubber plate, and a foam plate.

Basically, it suffices that the hinge portions constituting the protective band body foldably couple the multiple divided components to each other therebetween, and hence the following may be used therefor: rubber plate members having stretching properties provided between the divided components having rigidity, members sandwiching the hinge portions made of woven cloth or the like, or alternatively, members provided with hinge portions formed of a hinge or the like between the divided components. Thus, the material therefor is not particularly limited. It is preferable that the hinge portions be formed of opposite edge portions, which are opposite to each other, of the divided components adjacent to each other, and formed of bending portions which are formed between the opposite edge portions and extend in a width direction of the protective band body, and with which the protective band body is bent in a folding direction except when in use. As described above, the hinge portions are formed of the opposite edge portions and the bending portions, whereby the opposite edge portions are collided against each other in a butting manner so as to achieve substantially a non-divided state in which the protective band body constituted by the multiple divided components are not divided when in use. As a result, a preferable use state can be achieved and maintained.

In this context, it suffices that the hinge portions as described above are provided with the bending portions formed between the opposite edge portions, which are opposite to each other, of the divided components, extending in a width direction of the protective band body, and with which the protective band body is bent in a folding direction except when in use, and hence the structure thereof is not particularly limited. Typical examples of the hinge portions include, when the protective band body is formed of a single plate member, ones formed of process traces of slitting, notching, machining, or embossing which is effected on a front surface and/or a rear surface of the plate member which forms the protective band body. Further, for example, when the protective band body is formed as a laminated body including multiple main body layers which are separated from each other so as to form the divided components and a hinge layer for coupling those multiple main body layers to each other, the hinge portions formed in the protective band body include opposite edge portions, which are opposite to each other, of the main body layers adjacent to each other, and the hinge layer positioned between the opposite edge portions so as to form the bending portions. Still further, for example, the hinge portions include the opposite edge portions, which are opposite to each other, of the divided components adjacent to each other, and a hinge which is attached between the opposite edge portions and constitutes one of the bending portions. Yet further, for example, the hinge portions include a hinge which is attached between the divided components adjacent to each other and forms one of the bending portions, the hinge being provided with the opposite edge portions which are opposite to each other and constitute the hinge portions. Alternatively, when the protective band body is formed as a laminated body including the multiple main body layers and the hinge layer, the laminated body may be formed by bonding the multiple main body layers to one of surfaces or both the surfaces of the hinge layer, or in contrast, may be formed by bonding the hinge layer to one of surfaces or both the surfaces of each of the multiple main body layers.

Further, when the hinge is attached between the divided components of the protective band body so as to constitute the hinge portions, a hinge of any mode can be adopted. Preferred examples of the hinge include a sheet-like hinge in which the hinge itself is formed of the single plate member and the process traces of slitting, notching, machining, or embossing are formed in the front surface and/or the rear surface of the plate member so as to form the bending portions, and a sheet-like hinge in which the hinge itself is formed of a laminated body including the multiple (normally paired) main body layers separated from each other and the hinge layer for coupling those multiple main body layers to each other, the hinge layer being positioned between the opposite edge portions, which are opposite to each other, of the main body layers adjacent to each other, so as to form the bending portions. It is preferable that the sheet-like hinge as described above be formed in an appropriate size so as to extend in the width direction of the protective band body, thereby being attached between the divided components of the protective band body. Further, examples of the material constituting the sheet-like hinge include the materials similar to those constitutes the above-mentioned protective band body. In this case, the sheet-like material constituting the protective band body and the sheet-like material constituting the hinge may be integrally formed with each other so that the protective band body is manufactured by being cut out from the sheet-like material and, at the same time, that the sheet-like hinge is cut out therefrom. In addition, through adoption of the sheet-like hinge, the thickness of the protective band body can be reduced when being folded.

Further, in order to prevent reduction in rigidity of the protective band body which is divided into the multiple divided components when in use, it is preferable that some measures be taken such that the divided components constituting the protective band body may exert sufficient rigidity when in use of the protective band body, the measures including variation of the material and the thickness thereof, provision of multiple rib-like linear protrusions extending in the width direction of the protective band body, and adoption of two-layer structure to necessary portions. It is more preferable that the opposite edge portions of the divided components or of the main body layers, which form the hinge portions, be formed as rib portions having thicknesses larger than thicknesses of general portions of the divided components or of the main body layers.

Further, it is preferable that the bending portions of the hinge portions be positioned on an outer surface side in a thickness direction of the protective band body, the cervical vertebra protective band be curved around the cervical portion of the user without being bent at the bending portions when in use; and the cervical vertebra protective band be bent at the bending portions so as to be folded while an inner surface side of the thickness direction of the protective band body is exposed to an outer side except when in use. With this structure, without taking special measures for preventing the reduction in rigidity to the divided components of the protective band body, the rigidity of the protective band body constituted by the multiple divided components can be further increased when in use of the cervical vertebra protective band.

In addition, it is preferable that the multiple divided components constituting the protective band body and the hinge portions formed between the divided components be formed such that the folded divided components are substantially superimposed as much as possible on each other when the protective band body is folded with use of the hinge portions, and such that the entire flat surface area after the protective band body is folded is as small as possible. Alternatively, it is preferable that the protective band body be formed substantially symmetrically with respect to a center in the longitudinal direction thereof.

Further, when necessary, the divided components of the protective band body may include divided component bodies serving as a main body thereof and height adjustment members attached to the divided component bodies while being attachable/detachable. Through attachment/detachment of the height adjustment members, the dimension in the width direction of the divided components or the protective band as a whole may be adjustable. With this structure, even when the length of the cervical portion is different from user to user, the height adjustment can be easily performed through attachment/detachment of the height adjustment members with respect to the divided component bodies, adjustment of the attachment position in the width direction thereof, and the like.

In addition, it is preferable that the protective band body be provided with, over an entire surface and/or at both edge portions on an inner surface side thereof which are held in contact with the cervical portion when in use, a cushion plate for preventing both edges of the protective band body from being held in direct contact with the cervical portion. It is more preferable that the cushion plate have protruding ends which have both edge portions protruding outward from both the edges of the protective band body, the protruding ends being deformed in conformity with a shape of a contact position with the cervical portion so as to cover both the edges of the protective band body when in use. Further, it is still more preferable that the protruding ends of the cushion plate be inclined or bent in advance to a predetermined position toward the direction of covering both the upper and lower edges of the protective band body such that the protruding ends are easily deformed in conformity with the shape of the cervical portion so as to fit thereto when the user wears the cervical vertebra protective band.

In this context, regarding the mode of the protruding ends of the cushion plate which protrude outward from both the edges of the protective band body, it suffices that the protruding ends protrude by a length for covering both the upper and lower edges of the protective band body at least when in use. In the modes of other examples, the protruding ends protrude from the edges of the protective band body by a length of substantially 3 to 40 mm, preferably protrude by a length of 5 to 25 mm, or protrude by a length equal to or larger than the thickness of the protruding ends of the cushion plate. Further, in the modes of still other examples, the protruding ends protrude from the edges of the protective band body by a uniform width or nonuniform widths, protrude from the entire periphery of the protective band body, protrude from the center of the protective band body to the ends in a gradually decreasing manner, or protrude only in the vicinity of the center of the protective band body. Still further, in the modes of yet other examples, the protruding ends protruding from both the edges of the protective band body largely protrude, compared with other portions, from the portion which is in the vicinity of the center of the protective band body and extends over the length substantially one third of the entire length of the protective band body, or protrude by different lengths from the upper and lower edges of the protective band body.

Further, examples of the material of the cushion plate include a flexible material excellent in cushioning performance, which is formed of elastic rubber or plastic, or foam rubber or plastic, and a material of a plate-like body formed of those materials and into a single layer or multiple layers so as to have a uniform thickness or nonuniform thicknesses of substantially 1 to 50 mm. Examples of the material formed into the multiple layers include a laminated body formed solely of elastic rubber or plastic, a laminated body formed solely of foam rubber or plastic, and a laminated body formed any of elastic rubber or plastic, or foam rubber or plastic.

Further, regarding the protective band body, it is preferable that, in order to achieve preferable ventilation around the cervical portion when in use so as to increase fitting comfort and to achieve weight saving and improvement of the portability, the protective band body be provided with opening portions which pass through front and rear surfaces of the protective band body, the opening portions being formed in a region except the hinge portions of the protective band body. As long as enabling ventilation between the inside and outside of the protective band body, the opening portions are not particularly limited in shape, size, arrangement, and the like. Examples of the arrangement of the opening portions include one in which multiple round opening portions are arranged substantially vertically in the width direction of the protective band body, one in which one or multiple oval opening portions opening in the width direction are arranged substantially vertically in the width direction of the protective band body, and further, one in which those opening portions arranged in the width direction are arranged in multiple lines over the longitudinal direction of the protective band body. It is preferable that the opening portions arranged as described above be formed over the entire of the protective band body, and that substantially vertical multiple longitudinal ribs with which the upper and lower edge portions of the protective band body are coupled to each other in the width direction be formed while being remained. Thus, the reduction of the compressive resistance strength of the protective band body is preferably suppressed so that larger opening portions are formed.

In this context, regarding the opening portion which pass through the front and rear surfaces of the protective band body, the ratio of the area of the opening portions with respect to the surface area of the protective band body may be larger at the lateral sides with respect to the center of the protective band body. With this structure, suitable ventilation of the protective band body between the cervical portion and the outside can be achieved, and it is possible to set the compressive resistance strength in the width direction of the protective band body to be large at the center and small at the lateral sides. Thus, the compressive resistance strength can be secured at the center of the protective band body, and excellent connection of the fixing means for softening the lateral sides so as to hold the protective band body in the use state of being curved around the cervical portion can be achieved.

Further, regarding the protective band body described above, it is preferable that a flexible and attachable/detachable protective cover for covering substantially the entire thereof be prepared, that the protective cover be provided with holding means including engagement effected by belt-like bands to which hook/loop fasteners or the like for holding the folded protective band body in the folded state, stretchable rubber bands, or hooks are attached such that the protective cover is held in contact with the cervical portion of the user when in use, and that the cervical vertebra protective band is folded into a folded state by the holding means so as to be conveniently portable except when in use.

In the present invention, as long as being capable of maintaining the same shape of the protective band body as that in the use state thereof, the attachable/detachable fixing means for holding the protective band body in the use state thereof is not particularly limited. For example, the fixing means may include paired attachable/detachable portion such as hook/loop fasteners, male/female hooks, or male/female couplers, which are respectively attached to both the ends of the protective band body, the paired attachable/detachable portion as described above which are respectively attached to both the ends of the protective cover, or the paired attachable/detachable portion as described above one of which is attached to one end of the protective band body and the other end of which is attached to one end of the protective cover. In this context, any one of or both of this paired attachable/detachable portion may be attached to one end or both the ends of the protective cover so as to serve, when being attached to the protective cover and the protective band body is folded, also as a part of or the entire of the holding means for holding the protective band body in the folded state thereof.

Description of Reference Numerals

The folding cervical vertebra protective band according to the present invention has, for example, high compressive resistance strength sufficient for standing to some extent the large forward pressure applied to the cervical portion in proportion to the weight of the head at the time of a rear-end accident or the like of automobiles, and has a sufficient cervical vertebra protective function. In addition, the folding cervical vertebra protective band has the divided components obtained as a result of multiple divisions in the longitudinal direction of the protective band body thereof, and has the hinge portions for foldably coupling the multiple divided components to each other therebetween. With this structure, the entire of the folding cervical vertebra protective band is curved around the cervical portion and attached to the cervical portion when in use, and can be folded into a smaller size in two, three, or more at the hinge portions except when in use. As a result, the folding cervical vertebra protective band can be easily accommodated in a handbag or a pocket of a suit, and hence the portability thereof is remarkably increased. As a result, in a preventative view and for the safety, for example, mildly-ill patients or the like can always carry the folding cervical vertebra protective band in a bag, a handbag, a pocket of a suit, or the like when necessary.

Effects Of The Invention

The folding cervical vertebra protective band according to the present invention not only has the sufficient cervical vertebra protective function, but also can be easily folded into a conveniently portable size.

Figure 1:
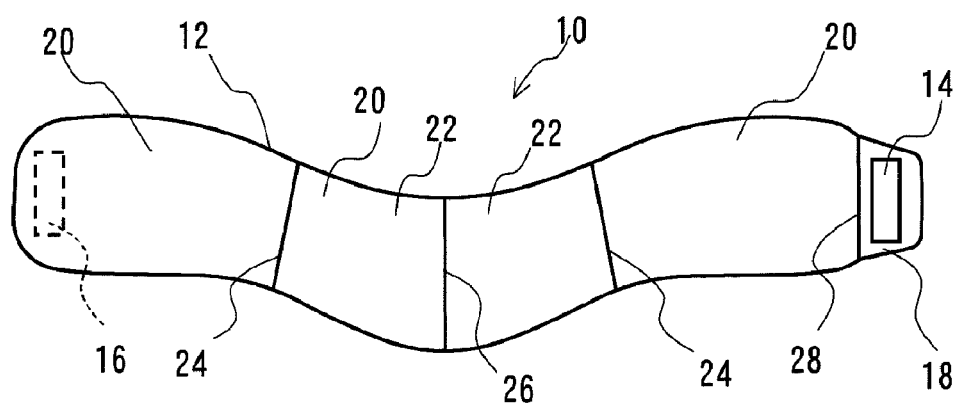
FIG. 1 is a front view illustrating a developed state of a folding cervical vertebra protective band according to a first embodiment of the present invention.

DESCRIPTION OF REFERENCE NUMERALS 10, 50, 60, 70, 100, 150, 200, 300, 400, 500, 600, 610, 620, 630, 650, 660, 670, 680, 700, 720: folding cervical vertebra protective band,
12, 52, 62, 72, 102, 152, 202, 302, 402, 502, 602, 612, 622, 632, 652, 662, 672, 682, 702, 722: protective band body,
14, 16: hook/loop fastener (paired attachable/detachable portion) (fixing means)),
20: triple-divided component (divided component),
22: subdivided component (divided component),
24, 26, 28: hinge portion,
30, 34, 38: opposite edge portion,
32, 36, 40: bending portion,
104, 105, 106, 108: main body layer,
110: hinge layer,
204, 663, 673, 675, 683: hinge,
304: rib portion,

404, 408: divided component body,
406, 410: height adjustment member,
504, 604, 605, 634, 635, 654, 655, 657, 665, 684: cushion plate,
606, 636, 656, 666: protruding end,
511: notch,
608, 638, 658, 668, 678, 688: opening portion,
704, 724: protective cover,
706: holding means,
728, 730: hook/loop fastener (holding means)

BEST MODE FOR CARRYING OUT THE INVENTION

In the following, with reference to embodiments illustrated in the accompanying drawings, preferred embodiment modes of the present invention are specifically described.

[First Embodiment]

FIG. 1 to FIG. 7 illustrate a folding cervical vertebra protective band according to a first embodiment of the present invention.

FIG. 1 is a front view illustrating a developed state of the folding cervical vertebra protective band 10 according to this embodiment. The folding cervical vertebra protective band 10 includes a belt-like protective band body 12 which has a length and a width for surrounding substantially the entire of a cervical portion of a user, and attachable/detachable hook/loop fasteners 14 and 16 (paired attachable/detachable portions (fixing means)) for holding, when in use, the protective band body 12 in a use state in which the protective band body 12 is curved around the cervical portion. The protective band body 12 is provided with a protruding portion 18 protruding on the right end thereof. One of the hook/loop fasteners 14 and 16 is attached to a surface of the protruding portion 18 of the protective band body 12, and the other is attached to a rear surface of the left end of the protective band body 12.

The protective band body 12 has triple-divided components 20 (divided components) which are obtained as a result of a triple division of the entire of the protective band body 12 so as to have substantially the same length, and has subdivided components 22 (divided components) which are obtained as a result of a further dual division of a central one of the triple-divided components 20 positioned at the center thereof so as to have substantially the same lateral length.

Further, the protective band body 12 has hinge portions 24 for foldably coupling the triple-divided components 20 to each other. Still further, the protective band body 12 has a hinge portion 26 positioned at substantially the center of the protective band body, for foldably coupling the subdivided components 22 to each other. Yet further, the protective band body 12 has a hinge portion 28 for foldably coupling one of the triple-divided components 20 and the protruding portion 18 to each other.

Figure 2:
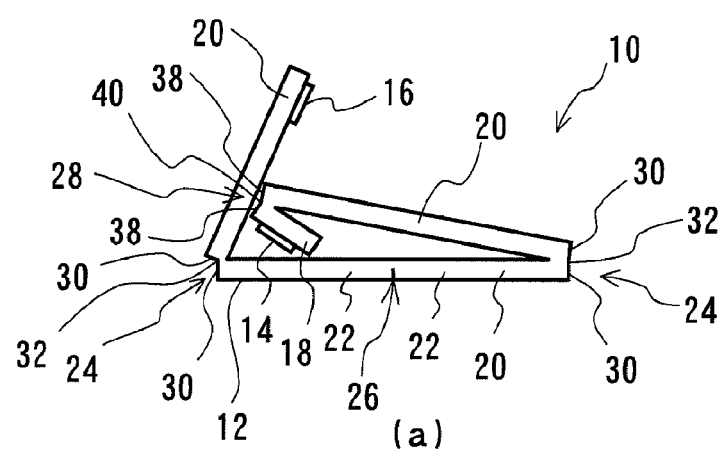
FIG. 2 are top views illustrating hinge portions of the folding cervical vertebra protective band according to the first embodiment of the present invention.

FIG. 2 are top views of the hinge portions 24, 26, and 28 of the folding cervical vertebra protective band 10. FIG. 2(a) is a top view illustrating a folded state in which the folding cervical vertebra protective band 10 is folded in three. FIG. 2(b) is a top view illustrating a folded state in which the folding cervical vertebra protective band 10 is folded in two. In FIG. 2(a), the hinge portions 24 are formed of opposite edge portions 30, which are opposite to each other, of the triple-divided components 20 adjacent to each other, and formed of bending portions 32 which are formed between the opposite edge portions 30, extend in a width direction of the protective band body 12, and is bent in a folding direction except when in use. In FIG. 2(b), the hinge portion 26 is formed of opposite edge portions 34, which are opposite to each other, of the subdivided components 22 adjacent to each other, and is formed of a bending portion 36 which is formed between the opposite edge portions 34, extends in the width direction of the protective band body 12, and is bent in the folding direction except when in use. The hinge portion 28 is formed of opposite edge portions 38, which are opposite to each other, of the one of the triple-divided components 20 and the protruding portion 18, and is formed of a bending portion 40 which is formed between the opposite edge portions 38, extends in the width direction of the protective band body 12, and is bent in the folding direction except when in use. Note that, in the hinge portions 24 of FIG. 1, the bending portions 32 extend in the width direction of the protective band body 12 while being inclined such that the lower portions thereof are exposed to the outer side. Therefore, the protective band body 12 is designed to be small in width and length when being folded in three with use of the hinge portions 24.

The hinge portions 24, 26, and 28 are formed of process traces of slitting effected on the surface of the plate member which forms the protective band body 12. The slitting in this embodiment represents the process traces formed as a result of slitting which is effected by a press-fitting device inserting a slitting blade to a predetermined depth and formed to have slit depths which are measured to be substantially 50% with respect to the thickness of the plate member from the surface thereof, the plate member forming the protective band body 12.

In this embodiment, the protective band body 12 is constituted by the triple-divided components 20 which are obtained as a result of the triple division of the entire of the protective band body 12 so as to have substantially the same length, and by the subdivided components 22 which are obtained as a result of the further dual division of the central one of the triple-divided components 20 so as to have substantially the same lateral length. However, note that the protective band body 12 can be constituted also by a pair of dual-divided components (divided components) which are obtained as a result of a dual division of the entire thereof so as to have substantially the same lateral length, or by multiple-divided components (divided components) which are obtained as a result of four or more divisions, of the entire thereof, and which have substantially the same length.

Figure 3:
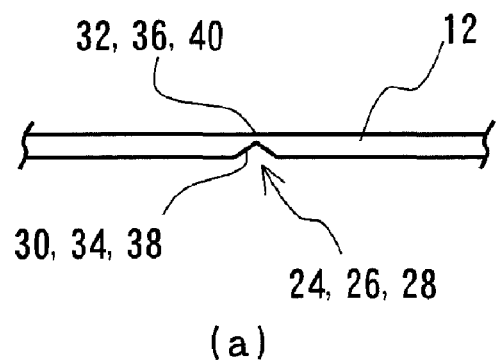
FIG. 3 are top views illustrating other examples of the hinge portions of the folding cervical vertebra protective band according to the first embodiment of the present invention.
Figure 3:
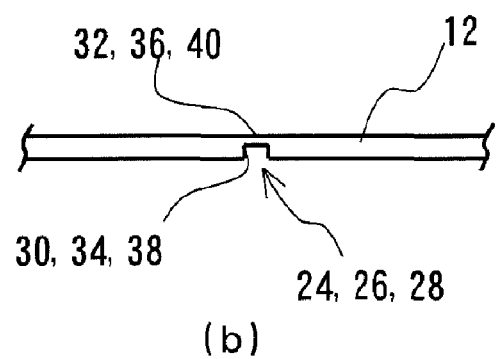
Figure 3:
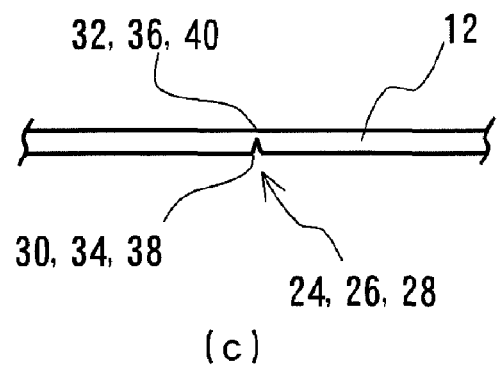

FIG. 3 are top views illustrating other examples of the hinge portions 24, 26, and 28 of the folding cervical vertebra protective band 10. In this embodiment, the hinge portions 24, 26, and 28 are formed of the process traces of the slitting effected on the surface of the plate member which forms the protective band body 12, and provided with the opposite edge portions 30, 34, and 38, and the bending portions 32, 36, and 40, respectively. However, as illustrated in FIG. 3, the hinge portions 24, 26, and 28 can be formed also of the process traces of notching effected on the surface of the plate member which forms the protective band body 12 (FIG. 3(a)), process traces of machining effected on the surface of the plate member which forms the protective band body 12 (FIG. 3(b)), or process traces of embossing effected on the surface of the plate member which forms the protective band body 12 (FIG. 3(c)). Regarding those process traces, in order to achieve high durability and excellent hinge properties, it is preferable that the process traces be formed to have slit depths which are measured to be substantially 30 to 70% with respect to the thickness of the plate member from the surface thereof, the plate member forming the protective band body.

Figure 4:
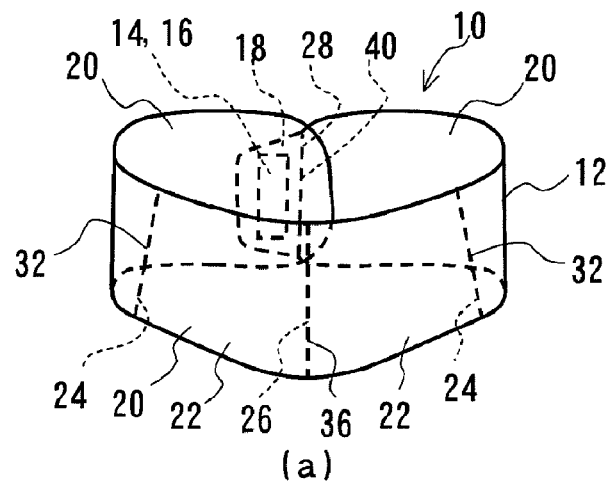
FIG. 4 are front views illustrating a use state and folded states of the folding cervical vertebra protective band according to the first embodiment of the present invention.
Figure 4:
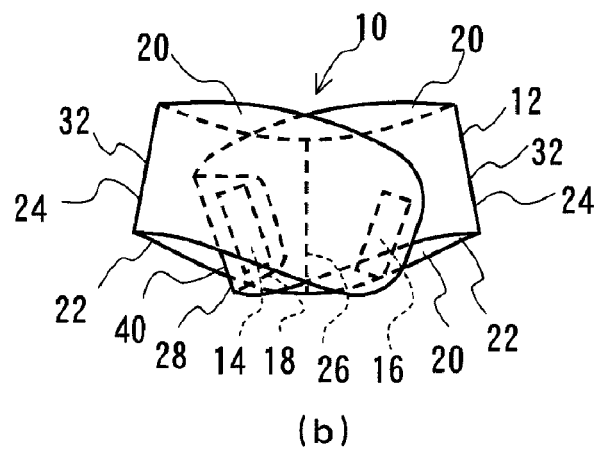
Figure 4:
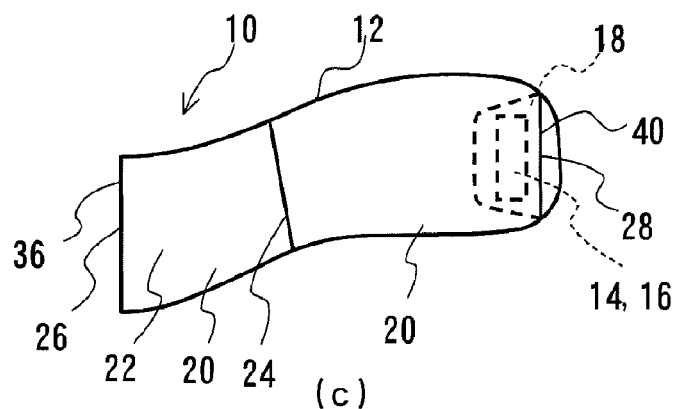

FIG. 4 are front views illustrating a use state and folded states of the folding cervical vertebra protective band 10 according to this embodiment. FIG. 4(a) is a front view illustrating the use state of the folding cervical vertebra protective band 10, when seen from the front thereof. FIG. 4(b) is a front view illustrating the folded state in which the folding cervical vertebra protective band 10 is folded in three. FIG. 4(c) is a front view illustrating the folded state in which the folding cervical vertebra protective band 10 is folded in two. The folding cervical vertebra protective band 10 is attached to the cervical portion while the entire thereof is curved around the cervical portion when in use, and is folded into a small size with use of the hinge portions 24, 26, and 28 except when in use. Specifically, the bending portions 32, 36, and 40 forming the hinge portions 24, 26, and 28 are positioned on the outer surface (surface exposed to the outer side when in use) side in the thickness direction of the protective band body 12. When in use, the opposite edge portions 30, 34, and 38 formed in the hinge portions 24, 26, and 28 are collided against each other in a butting manner so that the folding cervical vertebra protective band 10 is curved around the cervical portion of a user without being bent at the bending portions 32, 36, and 40, and except when in use, the folding cervical vertebra protective band 10 is bent at the bending portions 32, 36, and 40 so as to be folded in the direction opposite to the curved direction when in use, with the inner surface (surface exposed to the inner side when in use) side in the thickness direction of the protective band body 12 being on the outer side. Further, the protective band body 12 is formed substantially symmetrically with respect to the center in the longitudinal direction, and the hinge portions 24 for dividing the protective band body 12 into the triple-divided components 20 are formed such that the triple-divided components are substantially superimposed on each other when the protective band body 12 is folded with use of the hinge portions 24. Still further, the hinge portion 26 for dividing the protective band body 12 into the subdivided components 22 is formed such that the subdivided components are substantially superimposed on each other when the protective band body 12 is folded with use of the hinge portion 26. The folding cervical vertebra protective band 10 is formed such that the start point and the end point thereof are located right behind the cervical portion.

Note that, for the purpose of breathing of the cervical portion from the outside of the folding cervical vertebra protective band 10 when in use, the protective band body 12 can be provided with opening portions which are provided at appropriate portions of the protective band body 12 so as to pass the front and back thereof. It is preferable that the protective band body 12 be provided with the opening portions in terms of increasing comfort of the user in wearing the folding cervical vertebra protective band 10 and increasing portability as a result of weight saving. Therefore, it is preferable that the opening portions as large as possible be formed over the entire surface of the protective band body 12. When the opening portions are provided, the compressive resistance strength in the width direction of the protective band body 12 is reduced owing to the presence of the opening portions. Thus, it is preferable that the opening portions be configured and arranged while those factors are taken into account.

Note that, the protective band body 12 can be provided with, over the entire surface on the inner surface side and/or at both the edge portions thereof which are held in contact with the cervical portion at least when in use, cushion plates for preventing both the edges of the protective band body 12 from being held in direct contact with the cervical portion.

Note that, it is preferable that substantially the entire of the protective band body 12 be covered with a flexible and attachable/detachable protective cover, and further, it is preferable that the protective cover be provided with a holding means for holding the folded protective band body in the folded state.

Note that, it suffices that the protective band body 12 is attached to the cervical portion while the entire thereof is curved around the cervical portion, and hence the material therefor is not particularly limited. However, preferred examples of the material include: a synthetic resin which exhibits flexibility when being formed as a plate member, synthetic resin foam, rubber, or a laminated body formed of two or more of those materials selected therefrom; thermo plastic plastics, deformation-retaining plastics, elastomeric plastics rubbers, and rubbers; and plastics thereof; veneers each formed of rubber and foam plate thereof; laminate plates each obtained by laminating plastic plates each other; laminates each formed of a plastic plate and a rubber plate; laminates each formed of a plastic plate and a foam plate; and laminates each formed of combination of a plastic plate, a rubber plate, and a foam plate. The protective band body 12 of this embodiment is a plate-like body formed by sheet-extrusion molding of a syndiotactic 1,2-polybutadiene resin which is a thermoplastic elastomer. The protective band body 12 is formed to have substantially a thickness of 3 mm, a width of 7 cm, and the entire length of 51 cm, has both the appropriate flexibility and compressive resistance strength so as to exhibit excellent wearing comfort, and is lightweight so as to also exhibit excellent portability.

Figure 5:
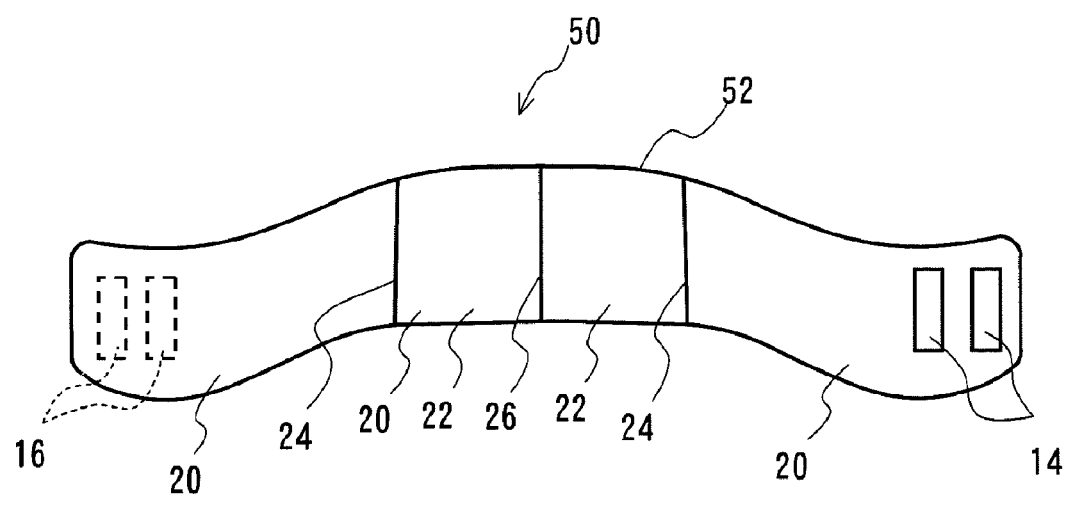
FIG. 5 illustrate a first modification of the folding cervical vertebra protective band according to the first embodiment of the present invention.
Figure 5:
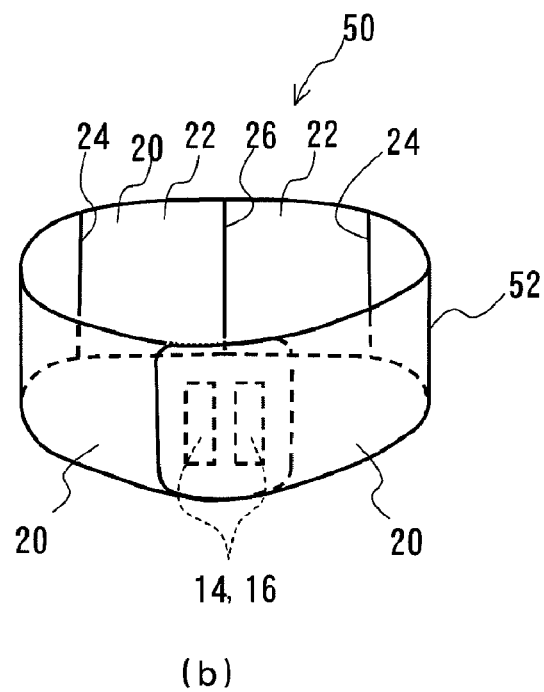

FIG. 5 illustrate a first modification of the folding cervical vertebra protective band 10 according to this embodiment. FIG. 5(a) is a front view illustrating a developed state of a folding cervical vertebra protective band 50. FIG. 5(b) is a front view illustrating a use state of the folding cervical vertebra protective band 50, when seen from the front thereof. The folding cervical vertebra protective band 50 is formed such that the start point and the end point thereof are located right in front of the cervical portion. Unlike the protective band body 12 of the folding cervical vertebra protective band 10, a protective band body 52 of the folding cervical vertebra protective band 50 is formed such that the start point and the end point thereof are located right in front of the cervical portion, the protruding portion 18 which is provided to the protective band body 12 is omitted, and the bending portions 32 (hinge portions 24) extend vertically in the width direction. Further, the two hook/loop fasteners 14 and the two hook/loop fasteners 16 are attached to both the lateral ends of the protective band body 52, respectively.

Figure 6:
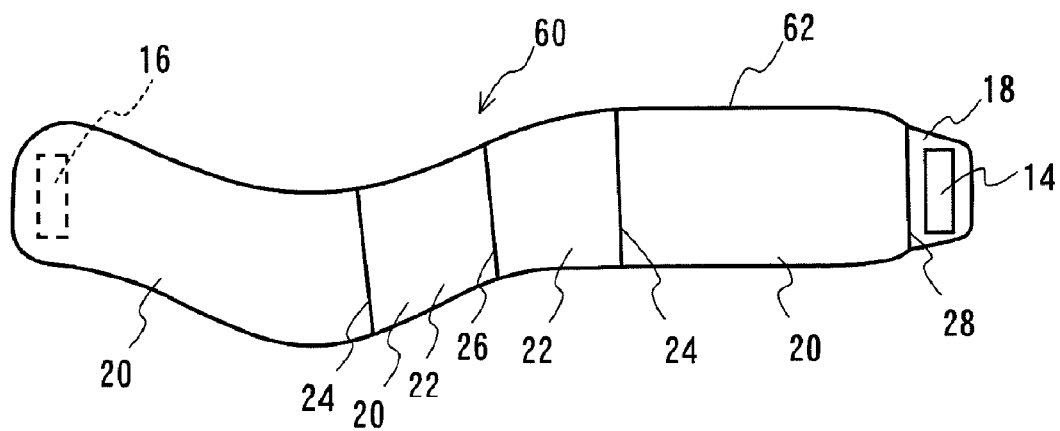
FIG. 6 illustrate a second modification of the folding cervical vertebra protective band according to the first embodiment of the present invention.
Figure 6:
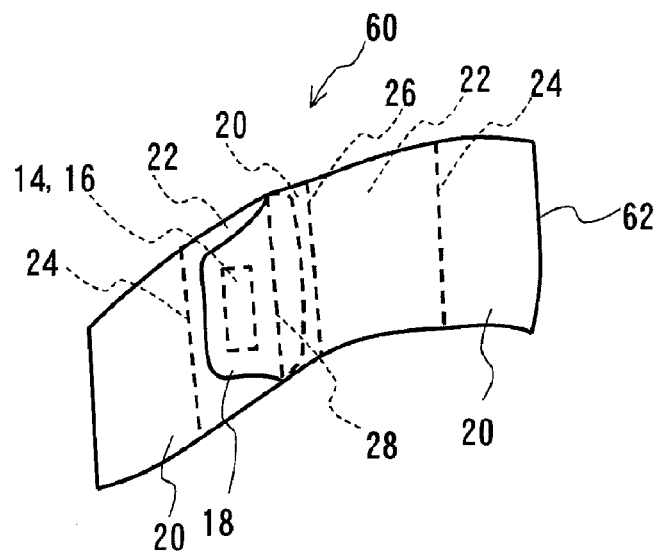

FIG. 6 illustrate a second modification of the folding cervical vertebra protective band 10 according to this embodiment. FIG. 6(a) is a front view illustrating a developed state of a folding cervical vertebra protective band 60. FIG. 6(b) is a front view illustrating a use state of the folding cervical vertebra protective band 60, when seen from the left side thereof. The folding cervical vertebra protective band 60 is formed such that the start point and the end point thereof are located right beside the cervical portion. Unlike the protective band body 12 of the folding cervical vertebra protective band 10, the protective band body 62 of the folding cervical vertebra protective band 60 is formed such that the start point and the end point thereof are located right beside the cervical portion, and the bending portions 32 (hinge portions 24) extend vertically in the width direction.

Figure 7:
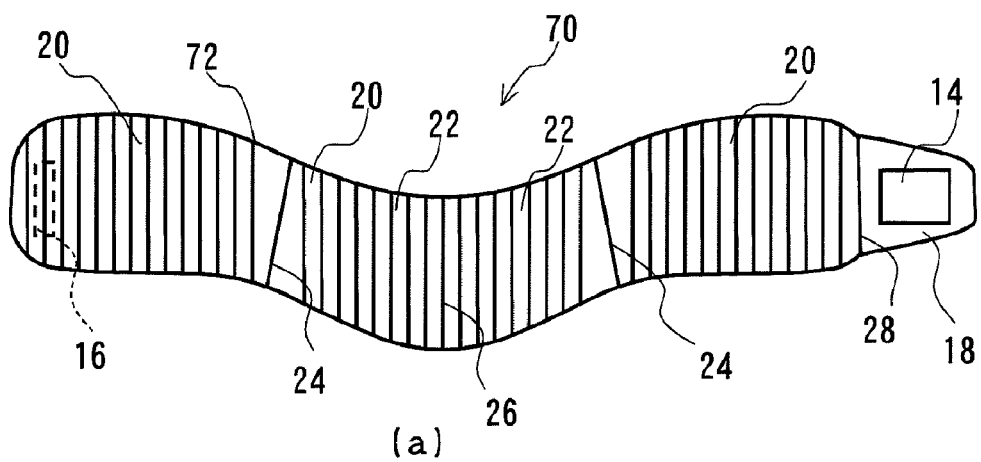
FIG. 7 illustrate a third modification of the folding cervical vertebra protective band according to the first embodiment of the present invention.
Figure 7:
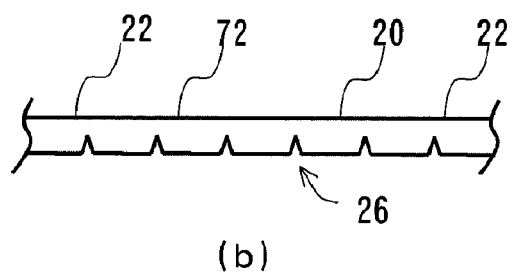
Figure 7:
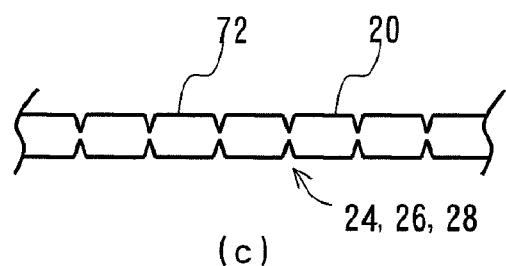
Figure 7:
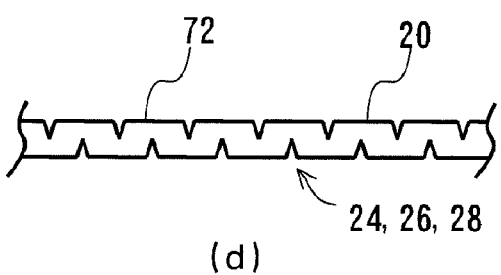

FIG. 7 illustrate a third modification of the folding cervical vertebra protective band 10 according to this embodiment. FIG. 7(a) is a front view illustrating a developed state of a folding cervical vertebra protective band 70. FIG. 7(b) is a partially enlarged top view illustrating a developed state of the center of the folding cervical vertebra protective band 70. Unlike the protective band body 12 of the folding cervical vertebra protective band 10, the hinge portions 24, 26, and 28 of the protective band body 72 of the folding cervical vertebra protective band 70 are formed of the process traces of embossing effected on the surface of the plate member which forms the protective band body 72. Further, on the surface of each of the triple-divided components 20 of the protective band body 72, the process traces are formed at uniform intervals by embossing effected vertically in the width direction thereof, the divided components being constituted by the subdivided components which are obtained as a result of further multiple divisions.

Note that, FIGS. 7(c) and 7(d) are partially enlarged top views illustrating applications of the protective band body 72 of the folding cervical vertebra protective band 70 in the developed states, which are replaceable therewith. In the figures, the process traces are provided by embossing effected on the surface of the plate member which forms the protective band body 72, and hence the hinge portions 24, 26, and 28 are formed. On the front and rear surfaces of each of the triple-divided components 20 of the protective band body 72, the process traces are formed at uniform intervals by embossing effected vertically in the width direction thereof, the divided components 20 being constituted by the subdivided components which are obtained as a result of further multiple divisions. Further, FIGS. 7(c) and 7(d) illustrate the process traces formed at different phases in the front and rear surface.

Note that, it is possible for the folding cervical vertebra protective band 70, in the use state thereof in which the protective band body 72 is curved around the cervical portion when in use, to easily bend the protective band body 72 in the longitudinal direction so as to facilitate the attachment thereof, and to easily effect the connection between the hook/loop fasteners 14 and 16 which are attachable/detachable and hold the protective band body 72 in the curved state, thereby ensuring the connectivity therebetween. Note that, when the hinge portions are formed on both the front and rear surfaces of the protective band body 72, the folding cervical vertebra protective band 70 can be folded at arbitrary positions, and further, can be folded in the directions of the front and rear surfaces in a Z-shaped manner or the like, other than a single direction in an L-shaped manner, an U-shaped manner, or the like.

[Second Embodiment]

Next, a second embodiment of the folding cervical vertebra protective band of the present invention is described. Note that, in this embodiment, the same constructions as those illustrated in the first embodiment are described while denoted by the same reference numerals, and description thereof is omitted.

Figure 8:
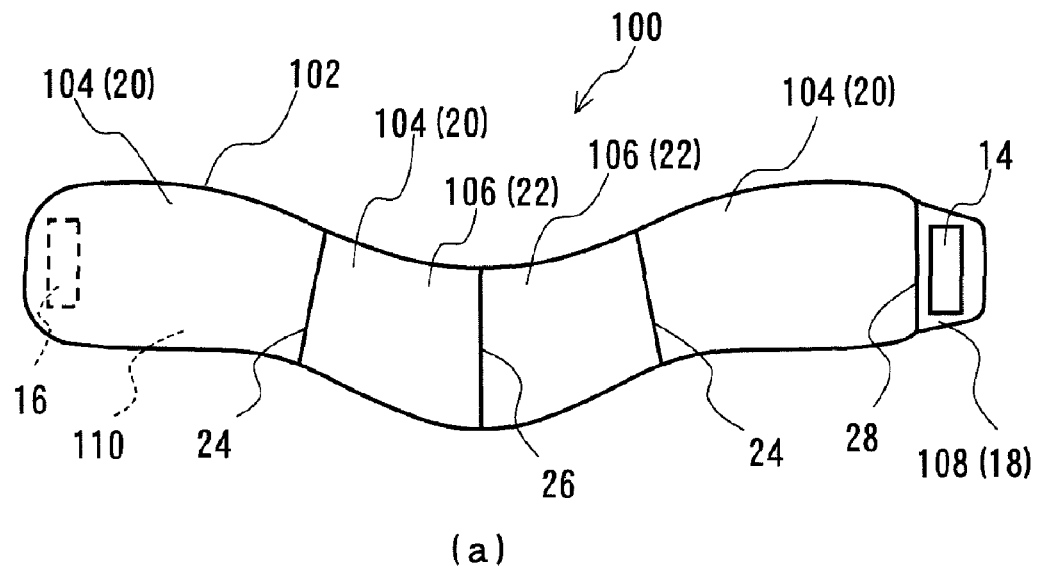
FIG. 8 illustrate a folding cervical vertebra protective band according to a second embodiment of the present invention.
Figure 8:
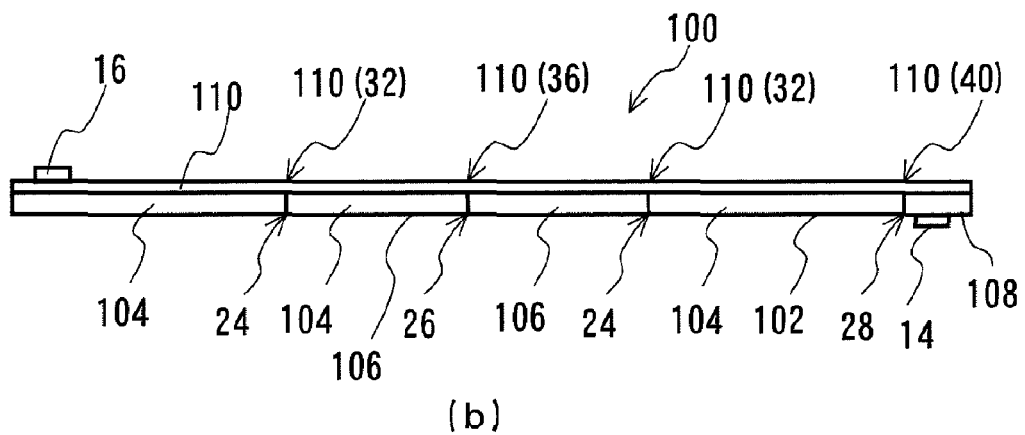
Figure 8:
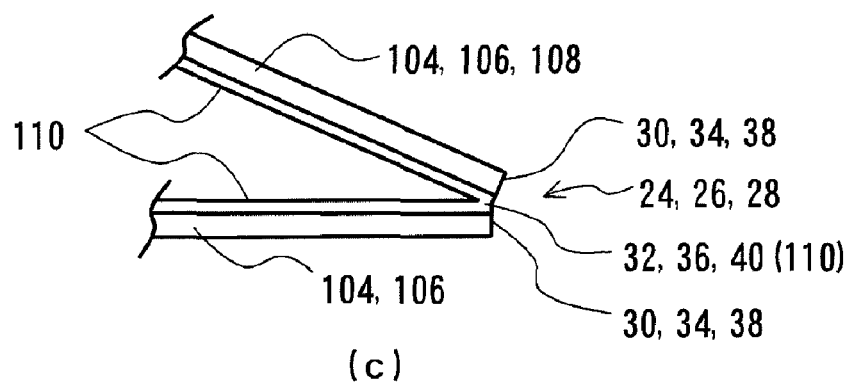
Figure 9:
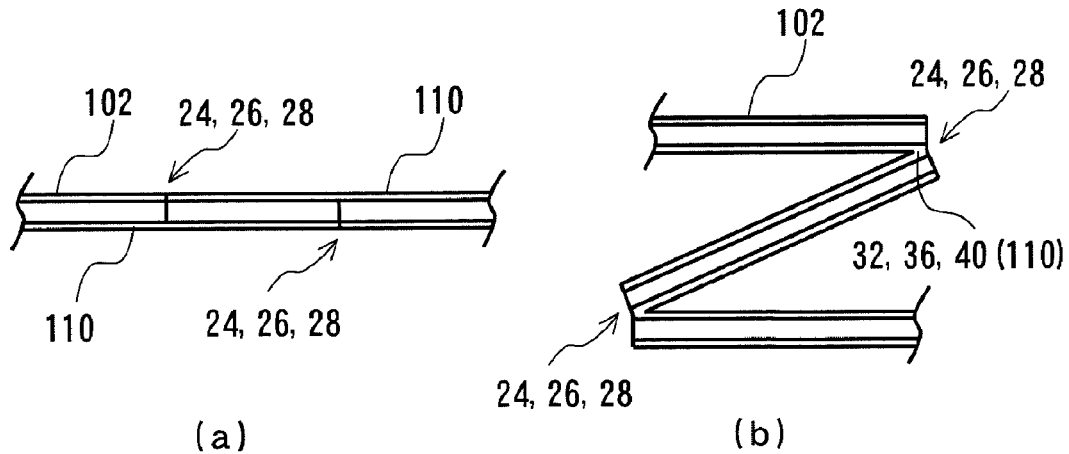
FIG. 9 are top views illustrating other examples of hinge portions of the folding cervical vertebra protective band according to the second embodiment of the present invention.
Figure 10:
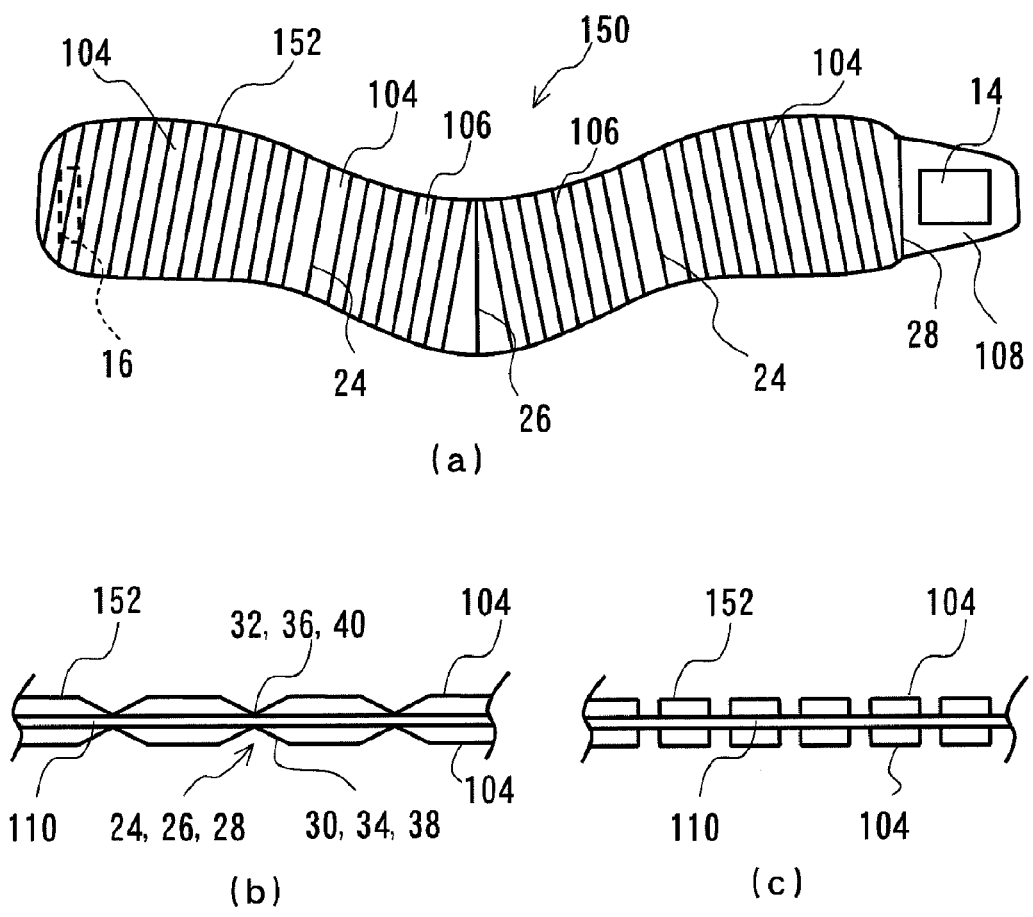
FIG. 10 illustrate a modification of the folding cervical vertebra protective band according to the second embodiment of the present invention.

FIGS. 8 to 10 illustrate a folding cervical vertebra protective band according to the second embodiment of the present invention.

FIG. 8 illustrate a folding cervical vertebra protective band 100 according to this embodiment. FIG. 8(a) is a front view illustrating a developed state of the folding cervical vertebra protective band 100. FIG. 8(b) is a top view illustrating a developed state of the folding cervical vertebra protective band 100. FIG. 8(c) is a partially enlarged top view illustrating a folded state of the folding cervical vertebra protective band 100. Unlike the protective band body 12 of the folding cervical vertebra protective band 10, the protective band body 102 of the folding cervical vertebra protective band 100 is formed as a laminated body including multiple main body layers 104 which form the triple-divided components 20, multiple main body layers 106 which form the subdivided components 22, a main body layer 108 which forms the protruding portion 18, and a hinge layer 110 for coupling the multiple main body layers 104, the multiple main body layers 106, and the main body layer 108 to each other. The following are positioned on the outer surface side in the thickness direction of the protective band body 102: the opposite edge portions 30, which are opposite to each other, of the main body layers 104 adjacent to each other through an intermediation of the hinge portions 24 formed in the protective band body 102, and a part of the hinge layer 110 which is positioned between the opposite edge portions 30 so as to form the bending portions 32; the opposite edge portions 34, which are opposite to each other, of the main body layers 106 adjacent to each other through an intermediation of the hinge portion 26 formed in the protective band body 102, and a part of the hinge layer 110 which is positioned between the opposite edge portions 34 so as to form the bending portion 36; and the opposite edge portions 38, which are opposite to each other, of one of the main body layer 104 and the main body layer 108 adjacent to each other through an intermediation of the hinge portion 28 formed in the protective band body 102, and a part of the hinge layer 110 which is positioned between the opposite edge portions 38 so as to form the bending portion 40. Note that, the laminated body is formed by bonding the multiple main body layers 104, the multiple main body layers 106, and the main body layer 108 to one surface of the hinge layer 110. The other constructions are the same as those of the first embodiment.

Note that, examples of the material of the hinge layer 110, which is excellent in hinge properties, include: plastics such as polypropylene, polyamide, polyethylene, and an ethylene vinyl acetate (EVA) copolymer; rubber elastomeric plastics such as a thermoplastic elastomer; deformation-retaining plastics each obtained by stretch processing of a polyethylene-based, polypropylene-based, polystyrene-based, polyamide-based, or polyester-based resin; thin plates each formed of polyvinyl chloride, polyurethane, and rubber; natural leather; artificial leather such as synthetic nonwoven cloth and vinyl leather; woven cloth such as sail cloth; woven cloth made of chemical fibers such as polyamide, polyester, vinylon, aramid, or carbon; and a thin plate obtained by impregnating a thermoplastic resin, rubber, or the like with a belt-like body as a base material, which is formed of those fibers extended and arranged in a single direction. Further, the hinge layer 110 of this embodiment is formed to have a thickness of 1 mm. As long as being capable of providing the hinge properties excellent in durability, the thickness of the hinge layer 110 is not particularly limited.

Further, the same material as that in the first embodiment can be applicable to the main layer. Note that, the laminated body of this embodiment is molded through heating and pressurizing plastic plates which form the polyethylene main body layers 104, 106, and 108 each having a thickness of 2 mm and polyester woven cloth, with an EVA-based thermoplastic film adhesive being sandwiched therebetween, impregnating the woven cloth made of chemical fibers with the thermoplastic film adhesive so as to form the hinge layer 110, and bonding the plastic plates which form the main body layers 104, 106, and 108 to the hinge layer 110 each other. Alternatively, the laminated body can be formed by impregnating the woven cloth made of chemical fibers with the thermoplastic film adhesive or rubber through heating and pressurizing so as to form the hinge layer 110 before bonding the plastic plates which form the main body layers 104, 106, and 108 thereto.

Note that, the hinge layer 110 of this embodiment is laminated over the entire one surface of the protective band body 102 so as to be formed as a hinge layer for coupling the multiple main body layers to each other and constituting the hinge portions of the protective band body 102. The hinge layer 110 which constitutes the protective band body can be provided in a size enabling the multiple main body layers to be foldably coupled to each other. For example, the hinge layer may be provided in a belt like manner over the entire surface or in a part of the protective band body in the width direction thereof at the portions around the hinge portions. Alternatively, it suffices that the hinge layer 110 is formed at least only at the portion enabling the multiple main body layers to be coupled to each other, for example, by being subjected to multiple divisions so as to be separated in the width direction. The protective band body 102 can be formed as the laminated body in the mode as described above.

FIG. 9 are partially enlarged top views illustrating the other examples of the hinge portions 24, 26, and 28 of the folding cervical vertebra protective band 100. The hinge portions 24, 26, and 28 of this embodiment are constituted by the laminated body including the multiple main body layers and the hinge layer 110 which is bonded to the one surfaces of the multiple main body layers forming the protective band body 102 so as to couple each of the main body layers to each other. However, the laminated body can be formed by bonding the hinge layers 110 to both surfaces of the multiple main body layers so as to constitute the hinge portions (FIG. 9(a)). With this structure, the hinge layers and the main body layers can be divided at the arbitrary portions of both the surfaces, whereby the folding cervical vertebra protective band 100 can be folded in an arbitrary direction, for example, folded in a Z-shaped manner (FIG. 9(b)).

FIG. 10 illustrate a modification of the folding cervical vertebra protective band 100 according to this embodiment. FIG. 10(a) is a front view illustrating a developed state of a folding cervical vertebra protective band 150. FIG. 10(b) is a partially enlarged top view illustrating a developed state of the folding cervical vertebra protective band 150. Unlike the protective band body 102 of the folding cervical vertebra protective band 100, a protective band body 152 of the folding cervical vertebra protective band 150 is formed as a laminated body in which the multiple main body layers 104, 106, and 108 are bonded to both the surfaces of the hinge layer 110, and the hinge portions 24, 26, and 28 formed in the protective band body 152 are formed of the opposite edge portions 30, 34, and 38, which are opposite to each other, of the main body layers 104, 106, and 108 adjacent to each other, and the hinge layer 110 which is positioned between the opposite edge portions 30, 34, and 38 so as to form the bending portions 32, 36, and 40. Further, the main body layers 104 (106) are constituted by the multiple main body layers which form subdivided components obtained as a result of further multiple divisions on both the surfaces of the hinge layer 110. Note that, the laminated body is formed by bonding the main body layers 104, the main body layers 106, and the main body layer 108 to both the surfaces of the hinge layer 110 which are obtained as a result of multiple divisions.

Note that, FIG. 10(c) is a partially enlarged top view illustrating similarly to FIG. 10(b) an application which is replaceable with the protective band body 152. In the figure, the main body layers forming the protective band body 152 are subjected to multiple divisions so as to be bonded to both the surfaces of the hinge layer 110, thereby being formed as a laminated body.

Note that, it is possible for the folding cervical vertebra protective band 150 of this modification, in the use state thereof in which the protective band body 152 is curved around the cervical portion when in use, to be easily bent in the longitudinal direction so as to facilitate the attachment thereof, and to easily conform to the shape of the cervical portion so as to easily effect the connection between the hook/loop fasteners 14 and 16 which are attachable/detachable and hold the protective band body 152 in the curved state. The folding positions of the folding cervical vertebra protective band 150 can be arbitrarily set, and the folding cervical vertebra protective band 150 can be folded in arbitrary directions.

[Third Embodiment]

Next, a third embodiment of the folding cervical vertebra protective band of the present invention is described. Note that, in this embodiment, the same constructions as those illustrated in the second embodiment are described while denoted by the same reference numerals, and description thereof is omitted.

Figure 11:
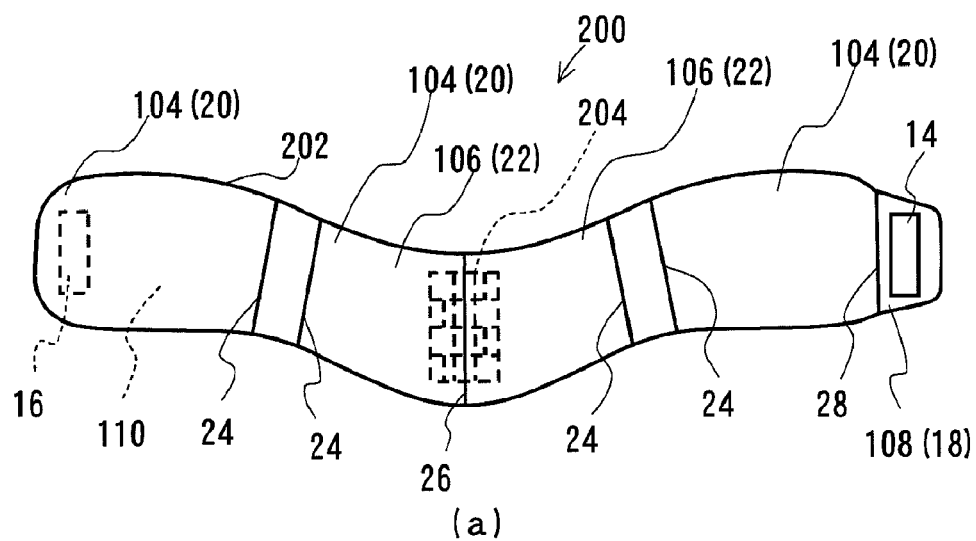
FIG. 11 illustrate a folding cervical vertebra protective band according to a third embodiment of the present invention.
Figure 11:
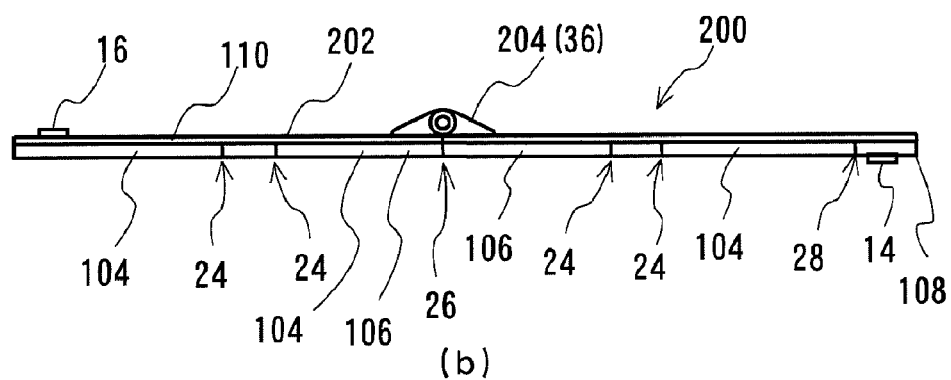
Figure 11:
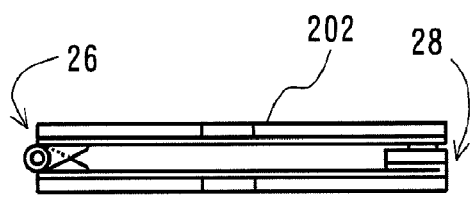
Figure 11:
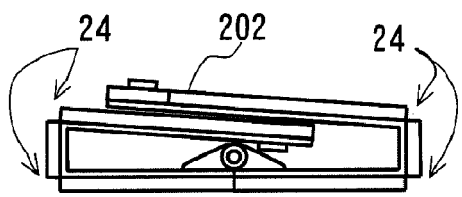

FIG. 11 illustrate a folding cervical vertebra protective band 200 according to the third embodiment. FIG. 11(a) is a front view illustrating a developed state of the folding cervical vertebra protective band 200. FIG. 11(b) is a top view illustrating the developed state of the folding cervical vertebra protective band 200. FIG. 11(c) is a top view illustrating a folded state in which the folding cervical vertebra protective band 200 is folded in two. FIG. 11(d) is a top view illustrating a folded state in which the folding cervical vertebra protective band 200 is folded in three.

Unlike the protective band body 102 of the folding cervical vertebra protective band 100, in a protective band body 202 of the folding cervical vertebra protective band 200, the following are positioned on the outer surface side in the thickness direction of the protective band body 202: the opposite edge portions 34, which are opposite to each other, of the subdivided components 22 adjacent to each other through an intermediation of the hinge portion 26; and a hinge 204 attached between the opposite edge portions 34 so as to constitute the bending portion 36. Note that, unlike the folding cervical vertebra protective band 100, in the folding cervical vertebra protective band 200, the hinge layer 110 is divided by the hinge portion 26 such that the protective band body 202 can be folded in two around the axial center of the hinge 204.

Further, unlike the folding cervical vertebra protective band 100, in the folding cervical vertebra protective band 200, two hinge portions 24 are formed by two portions of each of the hinge portions 24 parallel to each other at a predetermined interval. With this structure, when the folding cervical vertebra protective band 200 is folded in three, the thickness of one of the triple-divided components 20 on the other side can be accommodated within the C-shaped predetermined gap which is formed between two portions of each of the hinge portions 24 arranged at the predetermined interval. Therefore, the entire of the folding cervical vertebra protective band can be folded into a smaller size.

Note that, examples of the material of the hinge 204 include plastics such as polyamide. Examples of the means for attaching the hinge 204 to the hinge layer 110 include bonding, welding, screwing, and eyeletting. Note that, when the hinge 204 and the hinge layer 110 are made of the same material, the hinge 204 can be attached to the hinge layer 110 by high-frequency welding, spot welding with use of supersonic, or the like. In this embodiment, the hinge 204 made of polyamide plastic is preferably attached through heating and bonding onto the surface of the hinge layer 110 by the thermoplastic film adhesive.

Further, the following examples of the hinge 204 except one in this embodiment may be adopted as the hinge 204 according to this embodiment: a sheet-like hinge obtained by forming and cutting to an appropriate size the bending portions 32 and 36 which are formed with use of the process traces of slitting or the like effected on the sheet-like material which constitutes the hinge portions 24 and 26 of the protective band body 12 according to the first embodiment; or a sheet-like hinge obtained by forming and cutting to an appropriate size the bending portions 32 and 36 which are formed with use of the laminated body including two sheet-like materials which are separated from each other and constitute the hinge portions 24 and 26 of the protective band body 102 according to the second embodiment and the hinge layer. When the sheet-like hinge as described above is adopted, the thickness thereof can be reduced. Therefore, the thickness of the folding cervical vertebra protective band subjected to folding can be further reduced.

[Fourth Embodiment]

Next, a fourth embodiment of the folding cervical vertebra protective band of the present invention is described. Note that, in this embodiment, the same constructions as those illustrated in the second embodiment are described while denoted by the same reference numerals, and description thereof is omitted.

Figure 12:
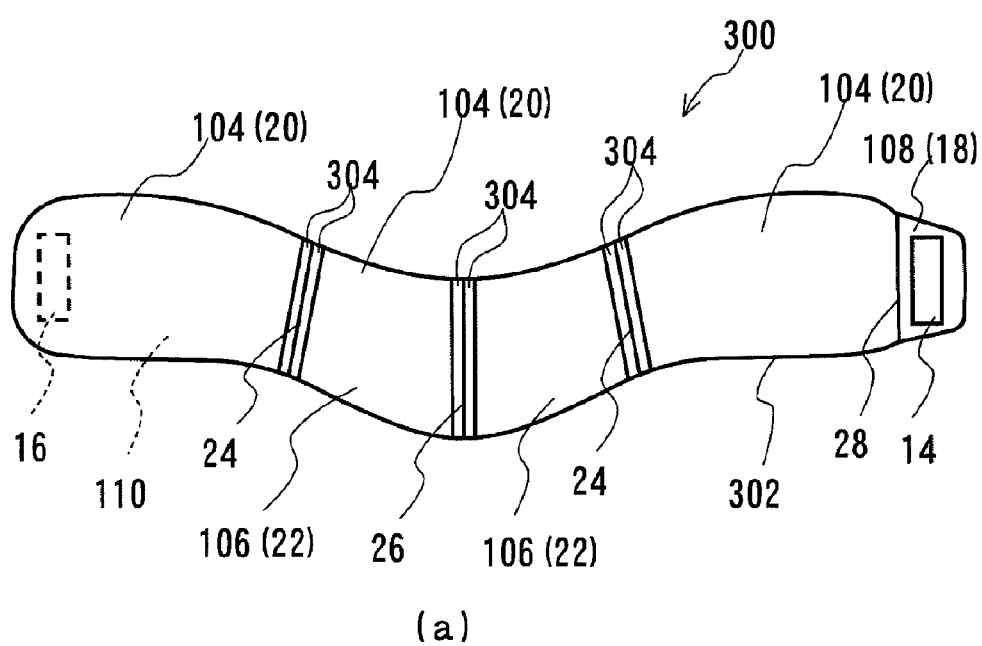
FIG. 12 illustrate a folding cervical vertebra protective band according to a fourth embodiment of the present invention.
Figure 12:
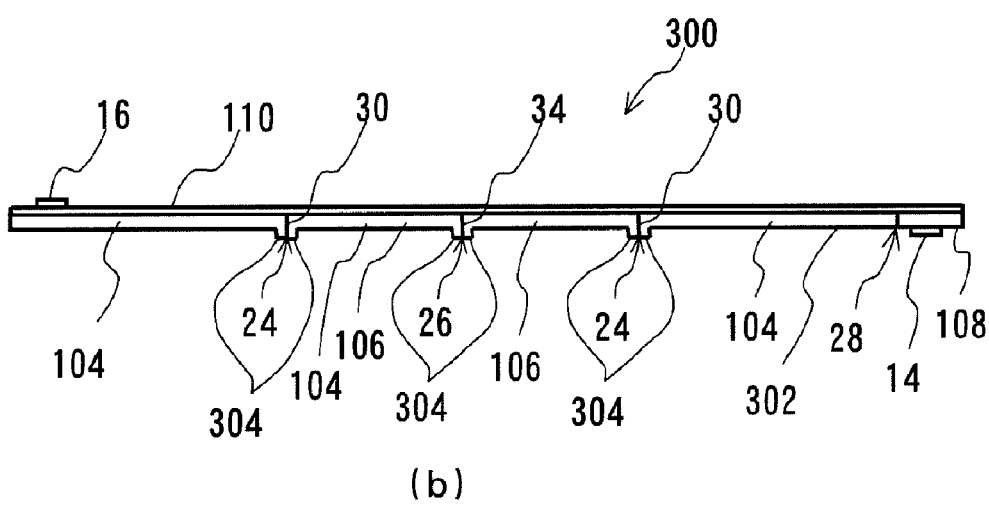

FIG. 12 illustrate a folding cervical vertebra protective band 300 according to this embodiment. FIG. 12(a) is a front view illustrating a developed state of the folding cervical vertebra protective band 300. FIG. 12(b) is a top view illustrating the developed state of the folding cervical vertebra protective band 300. Unlike the protective band body 102 of the folding cervical vertebra protective band 100, in a protective band body 302 of the folding cervical vertebra protective band 300, the opposite edge portions 30 of the main body layers 104, which form the hinge portions 24, and the opposite edge portions 34 of the main body layers 106, which form the hinge portion 26, are formed as rib portions 304 having thicknesses larger than the thicknesses of the general portions of the main body layers 104 and the main body layers 106.

Note that, unlike the protective band body 12 of the folding cervical vertebra protective band 10 according to the first embodiment, in the protective band body 302 of the folding cervical vertebra protective band 300, the opposite edge portions 30 of the triple-divided components 20, which form the hinge portions 24, and the opposite edge portions 34 of the subdivided components 22, which form the hinge portion 26, can be formed as the rib portions 304 having thicknesses larger than the thicknesses of the general portions of the triple-divided components 20 and the subdivided components 22.

Further, the rib portions 304 have an effect of increasing the compressive resistance strength in the width direction of the protective band body 302 which is formed to be relatively thin and lightweight, and are capable of increasing the colliding area of the opposite surfaces of the opposite edge portions 30 of the main body layers 104, which form the hinge portions 24, and the opposite edge portions 34 of the main body layers 106, which form the hinge portion 26. Thus, it is possible to prevent the abrasion and the deformation of the opposite edge portions 30 and 34 as a result of the collision therebetween during the repetitive use of the folding cervical vertebra protective band 300, thereby improving the durability of the hinge portions 24 and the hinge portion 26. Note that, while being formed over the entire of the protective band body 302 in the width direction thereof, the rib portions 304 in this embodiment may be formed in a part of the width direction, or may be formed by being subjected to multiple divisions in the width direction.

[Fifth Embodiment]

Next, a fifth embodiment of the folding cervical vertebra protective band of the present invention is described. Note that, in this embodiment, the same constructions as those illustrated in the first embodiment are described while denoted by the same reference numerals, and description thereof is omitted.

Figure 13:
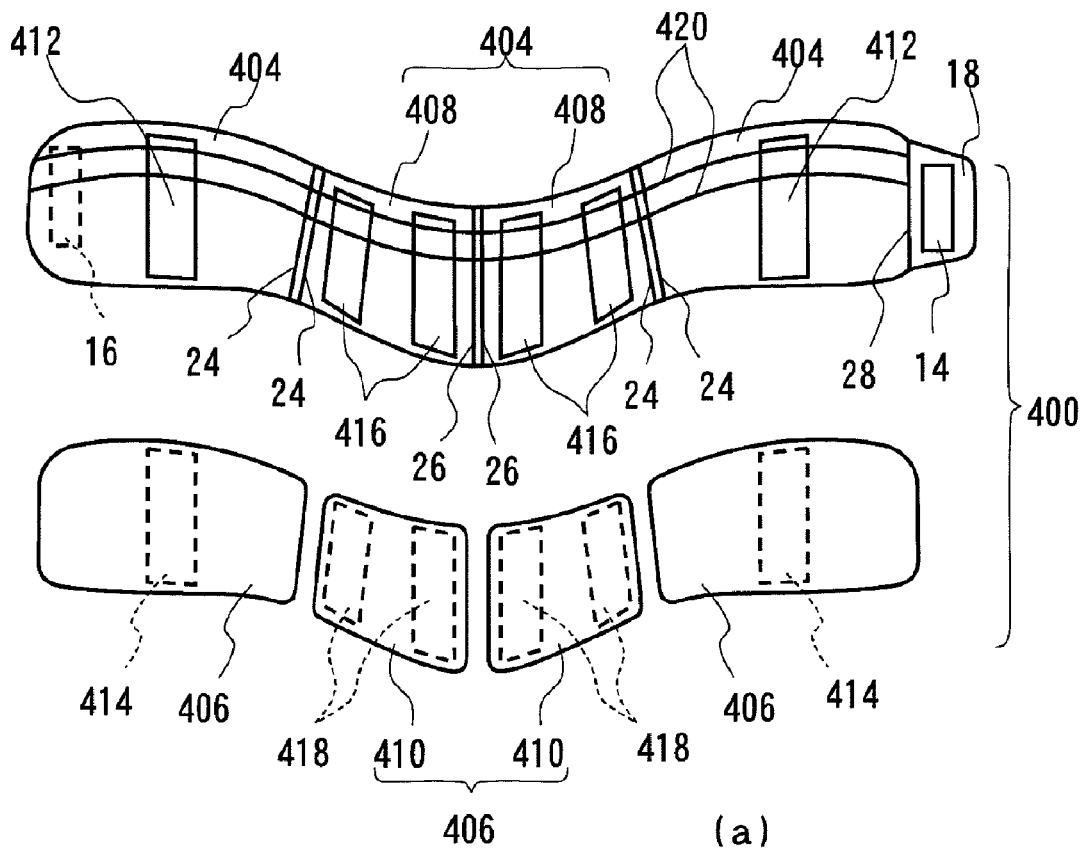
FIG. 13 illustrate a folding cervical vertebra protective band according to a fifth embodiment of the present invention.
Figure 13:
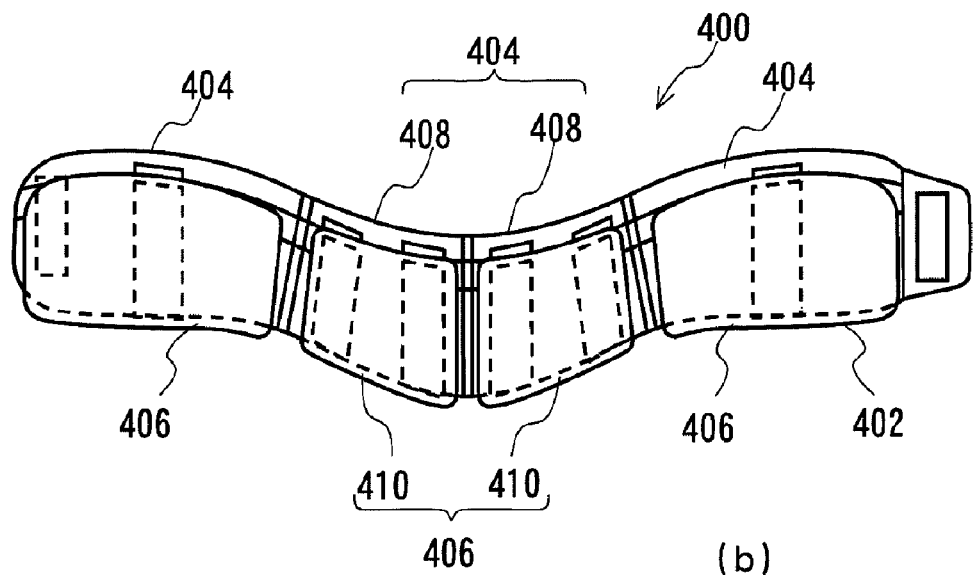

FIG. 13 illustrate a folding cervical vertebra protective band 400 according to this embodiment. FIG. 13(a) is a front view illustrating a developed state of the folding cervical vertebra protective band 400 before being assembled. FIG. 13(b) is a front view illustrating a developed state of the folding cervical vertebra protective band 400 after being assembled. Unlike the protective band body 12 of the folding cervical vertebra protective band 10, in a protective band body 402 of the folding cervical vertebra protective band 400, the triple-divided components 20 of the protective band body 402 are constituted by triple-divided component bodies 404 serving as the main body and height adjustment members 406 attached to the triple-divided component bodies 404 while being attachable/detachable and capable of adjusting the attachment positions in the width direction. The subdivided components 22 of the protective band body 402 are constituted by subdivided component bodies 408 serving as the main body and height adjustment members 410 attached to the subdivided component bodies 408 while being attachable/detachable and capable of adjusting the attachment positions in the width direction. Further, in the protective band body 402 of the folding cervical vertebra protective band 400, a hook/loop fastener 412 on one side is attached to the surface of each of the outer two of the triple-divided component bodies 404, a hook/loop fastener 414 on the other side is attached to the rear surface of each of the outer two of the height adjustment members 406, hook/loop fasteners 416 on one side are attached to the surface of each of the subdivided component bodies 408, and hook/loop fasteners 418 on the other side are attached to the rear surface of each of the height adjustment members 410. Still further, on the surfaces of the triple-divided component bodies 404 and the subdivided component bodies 408, there are formed auxiliary lines 420 for attaching the height adjustment members 406 and 410. Yet further, unlike the protective band body 12 of the folding cervical vertebra protective band 10, in the protective band body 402 of the folding cervical vertebra protective band 400, the two hinge portions 24 are formed by the two portions of each of the hinge portions 24 parallel to each other at the predetermined interval, and the hinge portion 26 is formed by the two portions of each of the hinge portions 26 parallel to each other at the predetermined interval.

Note that, the triple-divided component bodies 404 and the subdivided component bodies 408, and the height adjustment members 406 and the height adjustment members 410 are formed to have the thicknesses within the preferable range from 0.5 mm to 3 mm. The triple-divided component bodies 404 and the height adjustment members 406 except the hook/loop fasteners 412, 414, 416, and 418, and the subdivided component bodies 408 and the height adjustment members 410 are formed to have the total thicknesses within the preferable range from 1 mm to 6 mm, or within the more preferable range from 2 mm to 5 mm. Further, when the triple-divided component bodies 404 and the subdivided component bodies 408, and the height adjustment members 406 and the height adjustment members 410 have the thicknesses different from each other, the triple-divided component bodies 404 and the subdivided component bodies 408 are formed to have the thicknesses within the preferable range from 1 mm to 2.5 mm, and the height adjustment members 406 and the height adjustment members 410 are formed to have the thicknesses within the preferable range from 0.5 mm to 1.5 mm.

[Sixth Embodiment]

Next, a sixth embodiment of the folding cervical vertebra protective band of the present invention is described. Note that, in this embodiment, the same constructions as those illustrated in the first embodiment are described while denoted by the same reference numerals, and description thereof is omitted.

Figure 14:
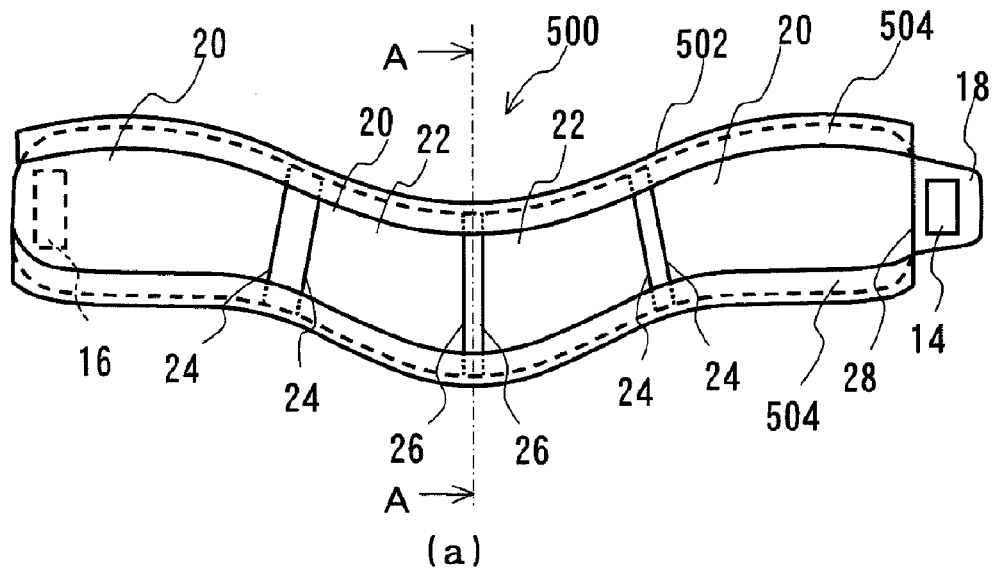
FIG. 14 illustrate a folding cervical vertebra protective band according to a sixth embodiment of the present invention.
Figure 14:
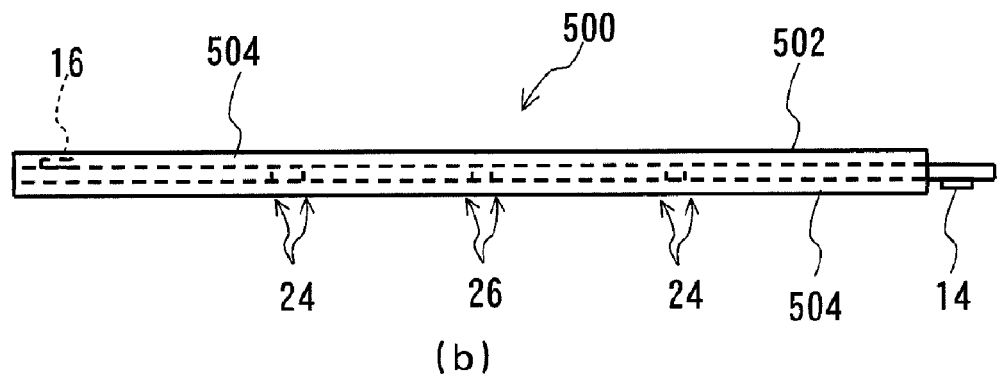
Figure 14:
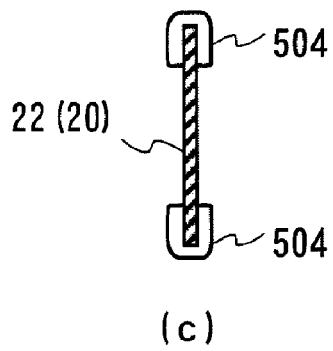
Figure 14:
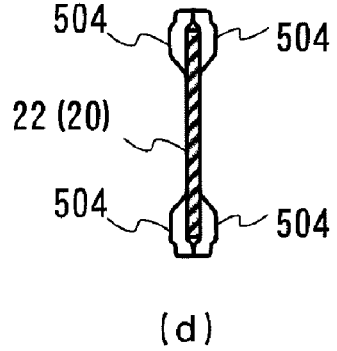
Figure 15:
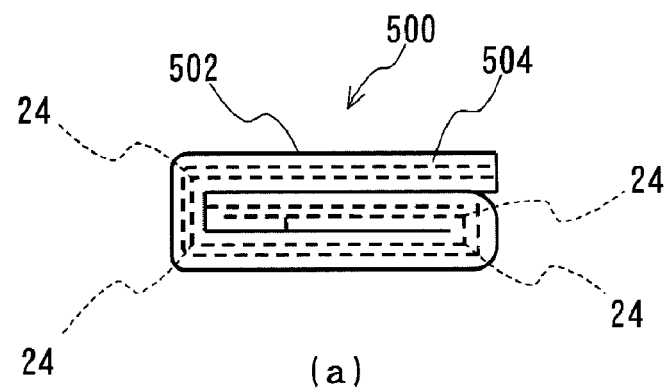
FIG. 15 are top views illustrating folded states of the folding cervical vertebra protective band according to the sixth embodiment of the present invention.
Figure 15:
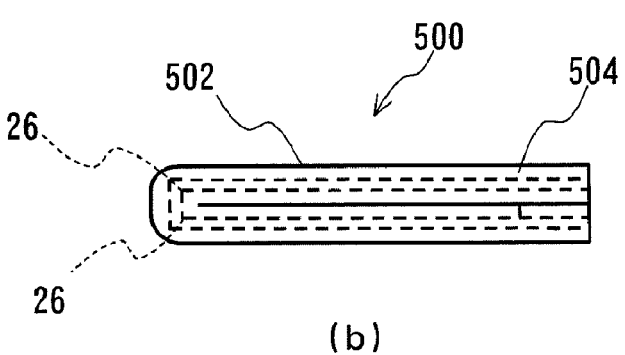

FIGS. 14 and 15 illustrate a folding cervical vertebra protective band 500 according to this embodiment. FIG. 14(a) is a front view illustrating a developed state of the folding cervical vertebra protective band 500. FIG. 14(b) is a top view illustrating the developed state of the folding cervical vertebra protective band 500. FIG. 14(c) is a sectional view taken along the line A-A of FIG. 14(a). FIG. 15(a) is a top view illustrating a folded state in which the folding cervical vertebra protective band 500 is folded in three. FIG. 15(b) is a top view illustrating a folded state in which the folding cervical vertebra protective band 500 is folded in two. Unlike the protective band body 12 of the folding cervical vertebra protective band 10, a protective band body 502 of the folding cervical vertebra protective band 500 is provided with, at both the edge portions thereof which are held in contact with the cervical portion when in use, cushion plates 504 for preventing both the edges of the protective band body 502 from being held in direct contact with the cervical portion. Further, unlike the protective band body 12 of the folding cervical vertebra protective band 10, in the protective band body 502 of the folding cervical vertebra protective band 500, the two hinge portions 24 are formed by the two portions of each of the hinge portions 24 parallel to each other at the predetermined interval, and the hinge portion 26 is formed by the two portions of the hinge portion 26 parallel to each other at the predetermined interval. Note that, FIG. 14(d) illustrates an application corresponding to FIG. 14(c), in which each of the cushion plates 504 include two cushion plates 504, which is replaceable with this embodiment.

Note that, preferred examples of the material of the cushion plates 504 include: an elastic material excellent in cushioning function, which is formed of elastic rubber or plastic, or foam rubber or plastic; that is, foam plastic such as polyethylene, an ethylene vinyl acetate copolymer, urethane, polystyrene, and silicone; foam synthetic rubber; foam natural rubber; polymer gel substance such as silicone and urethane; urethane rubber and vulcanized rubber which are excellent in elasticity; a urethane-based, silicone-based, or polyamide-based elastomeric elastomer resin; anyone of the above-mentioned resins or a composite thereof; a plate-like material formed to have a thickness of substantially 1 to 50 mm; and a plastic foam plate having expansion ratio of 10 to 50 times.

In this case, the cushion plates 504 are capable of increasing the wearing comfort when in use by covering both the upper and lower edges of the protective band body 502, which are relatively thin and have plate-like shapes, and capable of mitigating the shock applied when in use. Further, the cushion plates 504 having a predetermined thickness are provided at both the upper and lower edge portions of the protective band body 502, and hence a belt-like recessed portion is formed in the center of the protective band body 502 over the longitudinal direction thereof. The recessed portion forms a belt-like void portion between the cervical portion and the protective band body 502 when in use, to thereby constitute an inner surface vent path when in use with the result that the wearing comfort is further increased. Note that, the protective band body 502 can be provided also with the cushion plate 504 over the entire surface on the inner surface side thereof, which is held in contact with the cervical portion when in use.

Note that, the intervals between the two portions of the hinge portions 24 and the interval between the two portions of the hinge portion 26, which are formed in the protective band body 502, are determined based on the substantial maximum thickness and the folded thickness of the protective band body 502. In this embodiment, the interval between the two portions of the hinge portion 24 on the left side is larger than the intervals of the two portions of the other hinge portions, and the protective band body 502 can be compactly folded into a smaller size when folded in three. Note that, the hinge portions formed in the protective band body may include the hinge portions having one portion or the hinge portions having two or more portions. Further, those hinge portions can be formed in appropriate combinations in the protective band body.

Further, while the hinge portions 24 and the hinge portion 26 in this embodiment are provided with the process traces of slitting, the cushion plates 504 are not provided with those process traces. This is because, when the protective band body is folded, the flexible cushion plates can be extended in the hinge portions so as to follow the hinge portions. Thus, whether or not those process traces are formed in the cushion plates is arbitrary. In this embodiment, the protective band body 502 and the cushion plates 504 are bonded to each other by adhesive. However, the portions of the hinge portions 24 and the hinge portion 26 are not subjected to bonding over a predetermined width in the width direction. The cushion plates 504 can be easily extended in those portions. Note that, in the front and/or rear surfaces of each of the cushion plates 504, the process traces of slitting or the like can be formed similarly to the hinge portions 24 and 26. In this case, the restoration force of the cushion plates 504 upon being folded can be reduced.

Figure 16:
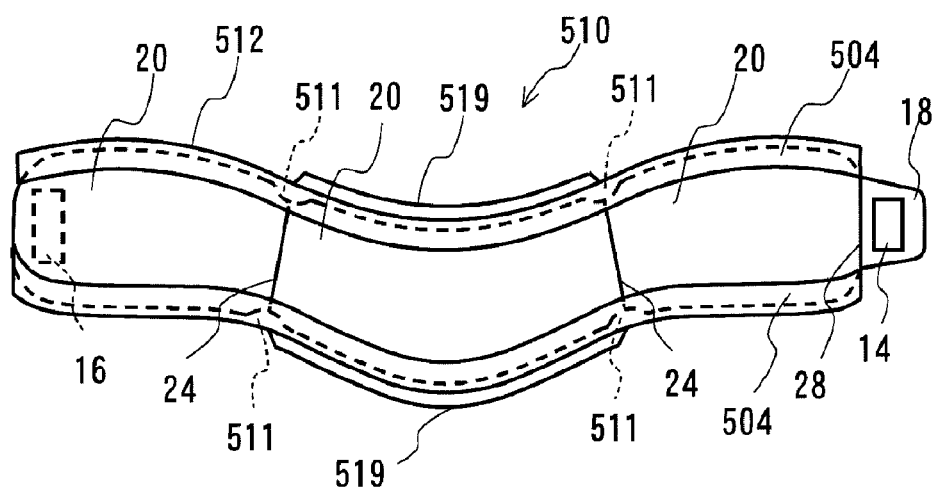
FIG. 16 illustrates a modification of the folding cervical vertebra protective band according to the sixth embodiment of the present invention.

FIG. 16 illustrates a modification of the folding cervical vertebra protective band 500 according to this embodiment. FIG. 16 is a front view illustrating a developed state of a folding cervical vertebra protective band 510 which is the modification of the folding cervical vertebra protective band 500. Unlike the protective band body 12 of the folding cervical vertebra protective band 10, a protective band body 512 of the folding cervical vertebra protective band 510 is provided with, at both the edge portions thereof which are held in contact with the cervical portion when in use, the cushion plates 504 for preventing both the edges of the protective band body 512 from being held in direct contact with the cervical portion. Further, unlike the protective band body 12 of the folding cervical vertebra protective band 10, the protective band body 512 of the folding cervical vertebra protective band 510 is constituted by the divided component bodies 20 serving as a main body thereof and height adjustment members 519 attached to the divided component bodies 20 while being attachable/detachable. Note that, the height adjustment members 519 are attached, while being attachable/detachable, to both the upper and lower ends of the cushion plates 504 which are provided at both the edge portions of the triple-divided components 20 of the protective band body 512. Further, the height adjustment members 519 are attached to one of the divided components 20, which is positioned at the center of the protective band body 512.

Then, the height adjustment members 519 are made of the same material as that of the cushion plates 504, and are formed in band-shapes having arbitrary heights in the widths approximate to the thicknesses of the cushion plates 504 at the upper and lower ends of the protective band body 512. The attachment/detachment of the height adjustment members 519 is effected with use of paired attachable/detachable members including a belt-like woven cloth piece (not shown) which is formed of loop-shaped fiber and bonded to the attachment surface of each of the cushion plates 504 of the protective band body 512, and a hook-shaped male fastener piece (not shown) which is attached to the attachment surface of each of the height adjustment members 519. Note that, with the height adjustment members 519 being detached therefrom, the protective band body 512 is designed to be formed of woven cloth which does not involve discomfort when in use, even when the belt-like woven cloth piece, which is formed of loop-shaped fiber and attached to each of the cushion plates 504 of the central one of the divided components 20, is held in direct contact with the cervical portion. In this case, the height adjustment members 519 may be formed so as to extend over the entire length of the protective band body 512, or may be singly formed on one of the upper and lower sides of the protective band body 512.

Further, the height adjustment of the protective band body 512 can be effected otherwise. For example, without forming the height adjustment members 519 to be attachable/detachable, the height adjustment members 519 having large heights are bonded by adhesive such as pressure-sensitive adhesive in advance so as to be cut as necessary, whereby the entire height of the protective band body 512 can be adjusted. In this case, it is desirable to apparently draw multiple cutting lines on the height adjustment members 519 in advance.

Note that, unlike the protective band body 12 of the folding cervical vertebra protective band 10, the protective band body 512 of the folding cervical vertebra protective band 510 is formed of the hinge portions 24 provided at two positions, which serve as the hinge portions 24 dedicated for being folded in three. In addition, notches 511 are formed at four positions in a part of both the edges of the protective band body 512, which constitute ends of the hinge portions 24. The notches 511 are provided for solving the problem of fitting discomfort at those portions upon wearing, the fitting discomfort being involved with loss of the uniformity of both the edges of the protective band body 512, which is caused by the hinge portions 24. The part of both the edges of the protective band body 512, which constitutes the ends of the hinge portions 24, is notched into an R-shape, whereby the wearing discomfort at those portions can be eliminated. Regarding the notch shape, it is preferable to adopt a circular-arc shape, a triangular shape, and the like, which are free from corner portions in addition.

Further, otherwise, in order to eliminate the wearing discomfort at both the edges of the protective band body 512 as described above when in use, the height near the center of the divided components 20 in the width direction thereof may be smaller than heights of the other portions, the center substantially corresponding to a lower jaw portion. Alternatively, both the edge portions of this portion may be thinner than those of the other portions, and further, the material of this portion may be replaced with a soft resin unlike that of the other portions. In this manner, the fitting feel with respect to the wearing discomfort sensed at the lower jaw portion, a chest, and the like can be improved.

[Seventh Embodiment]

Next, a seventh embodiment of the folding cervical vertebra protective band of the present invention is described. Note that, in this embodiment, the same constructions as those illustrated in the first embodiment are described while denoted by the same reference numerals, and description thereof is omitted.

Figure 17:
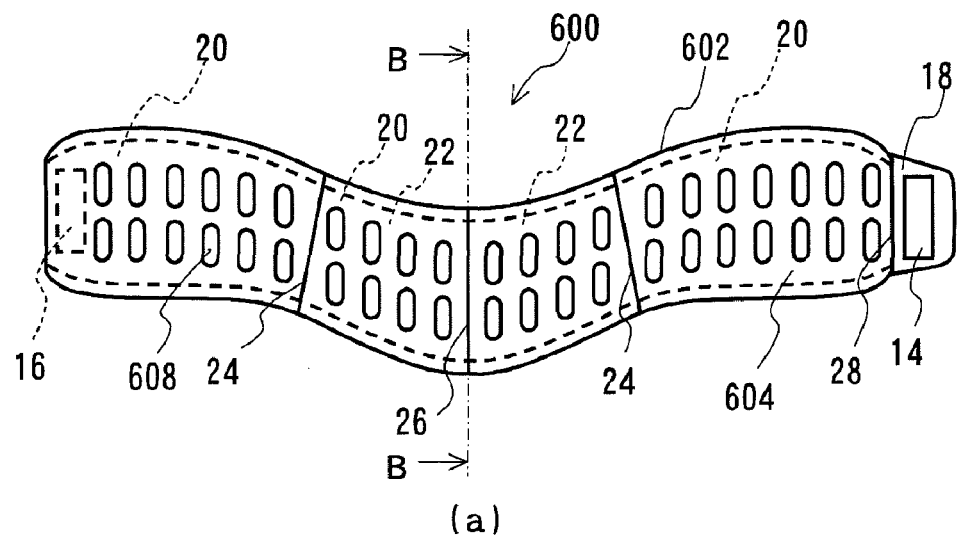
FIG. 17 illustrate a folding cervical vertebra protective band according to a seventh embodiment of the present invention.
Figure 17:
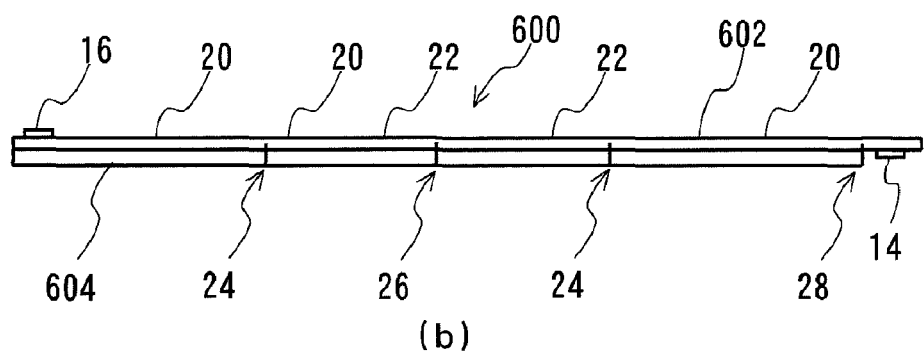
Figure 17:
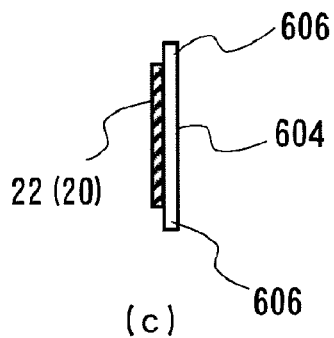
Figure 17:
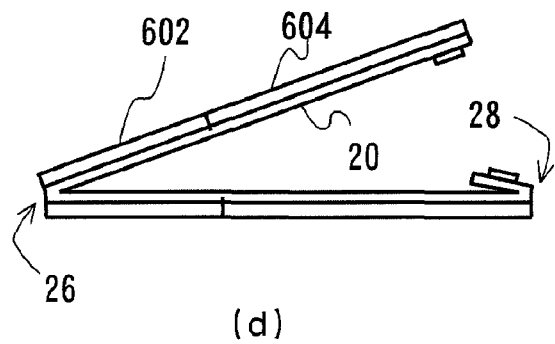

FIG. 17 illustrate a folding cervical vertebra protective band 600 according to this embodiment. FIG. 17(a) is a front view illustrating a developed state of the folding cervical vertebra protective band 600. FIG. 17(b) is a top view illustrating the developed state of the folding cervical vertebra protective band 600. FIG. 17(c) is a sectional view taken along the line B-B of FIG. 17(a). FIG. 17(d) is a top view illustrating a folded state in which the folding cervical vertebra protective band 600 is folded in two. Unlike the protective band body 12 of the folding cervical vertebra protective band 10, a protective band body 602 of the folding cervical vertebra protective band 600 is provided with, over the entire surface on the inner surface side thereof which is held in contact with the cervical portion at least when in use, a cushion plate 604 for preventing both the edges of the protective band body 602 from being held in direct contact with the cervical portion. The cushion plate 604 has protruding ends 606 which respectively constitute both edge portions protruding outward from both the edges of the protective band body 602. When in use, the protruding ends 606 are deformed in conformity with the shape of the contact position with the cervical portion so as to cover both the edges of the protective band body 602. Further, the hinge portions 24 and the hinge portion 26 of the protective band body 602 are formed of process traces effected from the surface of the protective band body 602 together with the cushion plate 604.

Note that, it is preferable that the protruding ends 606 of the cushion plate 604 be formed to have the length, when the cushion plate 604 is deformed when in use, sufficient for covering both the upper and lower edge portions of the protective band body 602, and protrude outward from both the edges of the protective band body 602 by the length of substantially 5 to 30 mm, more preferably, the length of 10 to 25 mm, or the length larger than the thickness of the cushion plate constituting the protruding ends 606. With this structure, both the edges of the protective band body 602 can be effectively covered. In addition, the protruding ends 606 may be provided only at the center of the protective band body 602 (center in the longitudinal direction, substantially one third of the entire length), or may be provided so as to gradually decrease the width from the center to the end. As the cushion plate 604, a cushion plate similar to the cushion plates 504 of the sixth embodiment can be used. Further, the cushion plate 604 of this embodiment is provided over the entire surface on the inner surface side which is held in contact with the cervical portion when in use. Therefore, excellent cushioning effect is exerted to any portion of the cervical portion, and comfort is increased. Note that, the cushion plate 604 may be provided only at both the upper and lower edge portions except the center in the width direction of the protective band body 602, or may be provided on both surface sides, for example, over the entire surface or on a part of the outer surface side of the protective band body 602, which is not held in contact with the cervical portion.

Note that, unlike the protective band body 12 of the folding cervical vertebra protective band 10, the protective band body 602 of the folding cervical vertebra protective band 600 is provided with opening portions 608 which pass through the front and rear surfaces of the protective band body 602 substantially over the entire surface of the protective band body 602. The opening portions 608 are formed in the region except the hinge portions of the protective band body 602. In addition, the opening portions 608 are formed as multiple ovals which have shapes of substantially elongated holes and pass through both the protective band body 602 and the cushion plate 604, and multiply arranged in a substantially vertical manner over the width direction of the protective band body 602. Further, the opening portions are arranged in multiple lines over the longitudinal direction of the protective band body 602. Note that, in the protective band body 602 provided with the opening portions, multiple vertical ribs with which the upper and lower edge portions are coupled to each other in the width direction are formed while being remained. Therefore, the reduction of the compressive resistance strength of the protective band body 602 is suppressed, whereby larger opening portions are formed so as to achieve suitable ventilation between the cervical portion and the outside when in use.

Figure 18:
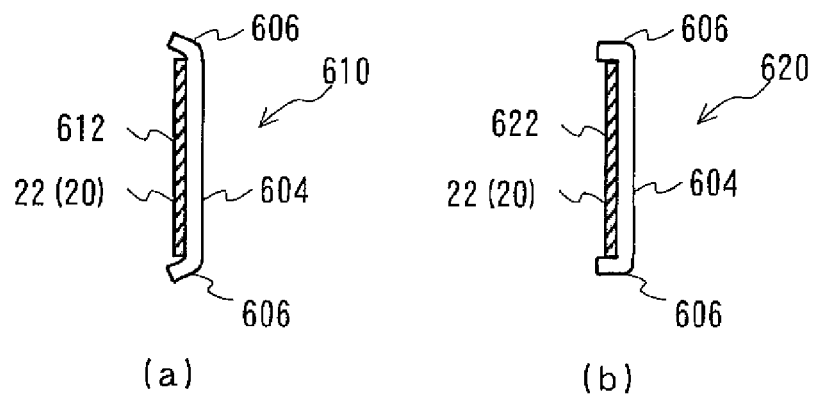
FIG. 18 illustrate a modification of the folding cervical vertebra protective band according to the seventh embodiment of the present invention.

FIG. 18 illustrate modifications of the folding cervical vertebra protective band 600 according to this embodiment. FIG. 18(a) is a sectional view illustrating, similarly to FIG. 17(c), a developed state of a folding cervical vertebra protective band 610 which is a first modification of the folding cervical vertebra protective band 600. As well, FIG. 18(b) is a sectional view illustrating, similarly to FIG. 17(c), a developed state of a folding cervical vertebra protective band 620 which is a second modification of the folding cervical vertebra protective band 600. Unlike the protective band body 602 of the folding cervical vertebra protective band 600, in a protective band body 612 of the folding cervical vertebra protective band 610, each of the protruding ends 606 of the cushion plate 604 is inclined in advance to the predetermined position to the direction of covering both the upper and lower edges of the protective band body. Unlike the protective band body 602 of the folding cervical vertebra protective band 600, in a protective band body 622 of the folding cervical vertebra protective band 620, each of the protruding ends 606 of the cushion plate 604 is bent in advance to the predetermined position to the direction of covering both the upper and lower edges of the protective band body.

Note that, the cushion plate 604 may include two or more cushion plates. For example, when the cushion plate 604 includes two cushion plates, the two cushion plates are bonded to the protective band body 612 or the protective band body 622 while being slid at the portions of the protruding ends 606, thereby being easily inclined or bent.

Figure 19:
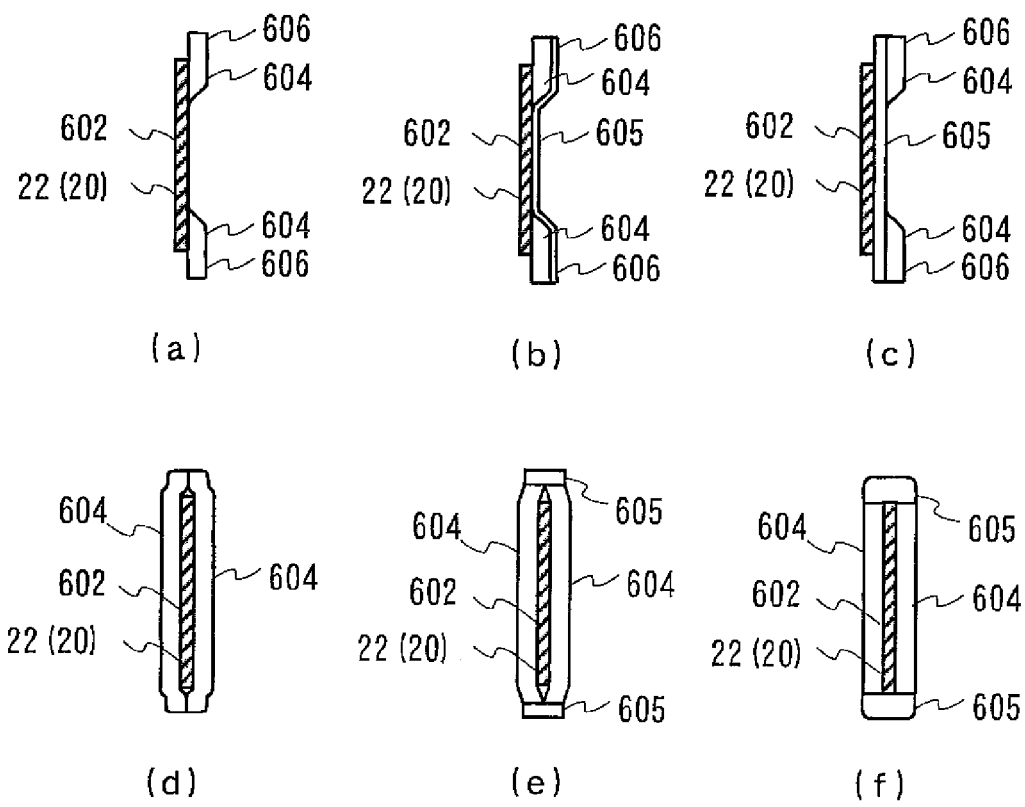
FIG. 19 illustrate arrangement examples of cushion plates of the folding cervical vertebra protective band according to the seventh embodiment of the present invention.

FIG. 19 are sectional views illustrating, similarly to FIG. 17(c), arrangement examples of the cushion plates to be provided to the protective band body 602 of the folding cervical vertebra protective band 600 according to this embodiment. FIGS. 19(a) to (c) illustrate examples of the cushion plates 604 provided separately from each other in the width direction of the protective band body 602. Specifically, FIGS. 19(b) and (c) illustrate examples of a second cushion plate 605 provided over the entire surface in the width direction of the protective band body 602. In addition, the protruding ends 606 are formed at both the edges of the protective band body 602 so as to protrude outward therefrom. The protective band body 602 is provided with, over the entire surface on the inner surface side and/or at both the edge portions thereof which are held in contact with the cervical portion at least when in use, the cushion plates 604 and/or the cushion plate 605 for preventing both the edges of the protective band body 602 from being held in direct contact with the cervical portion. Further, a belt-like recessed portion is formed over the longitudinal direction substantially in the center of the protective band body 602, whereby an inner surface vent path when in use is formed.

In this case, except the method of forming the recessed portion over the longitudinal direction substantially in the center of the protective band body 602 with use of the cushion plates 604 as described above which are provided separately from each other in the width direction of the protective band body 602, there may be given the following methods of forming the recessed portion by grinding off the center of the cushion plate having a size larger than that for covering the entire surface of the protective band body 602, forming the recessed portion by a cushion plate deformation means obtained by effects of heating, pressurizing, or chemical materials, and forming the recessed portion simultaneously with the molding of the cushion plate. The inner surface vent path when in use may be formed by adopting the cushion plate obtained by those methods.

FIGS. 19(d) to (f) illustrate examples of the cushion plates 604 formed over both the entire surfaces of the protective band body 602. Specifically, FIGS. 19(e) and (f) illustrate examples of the second cushion plate 605 formed at both the upper and lower edges of the protective band body 602. In addition, the protective band body 602 is provided with, over the entire surface on the inner surface side and/or at both the edge portions thereof which are held in contact with the cervical portion at least when in use, the cushion plates 604 and/or the cushion plates 605 for preventing both the edges of the protective band body 602 from being held in direct contact with the cervical portion. Note that, those arrangement examples of the cushion plates are suitably applicable to the other embodiments.

Note that, in the examples illustrated in FIGS. 19(d) to (f), when being formed to be larger (higher) in advance in the width direction than the divided components 20, the cushion plates 604 or the cushion plates 605 are cut thereafter in accordance with the cervical portion of the user, to thereby adjust the height in the width direction of the protective band body 602.

[Eighth Embodiment]

Next, an eighth embodiment of the folding cervical vertebra protective band of the present invention is described. Note that, in this embodiment, the same constructions as those illustrated in the second embodiment are described while denoted by the same reference numerals, and description thereof is omitted.

Figure 20:
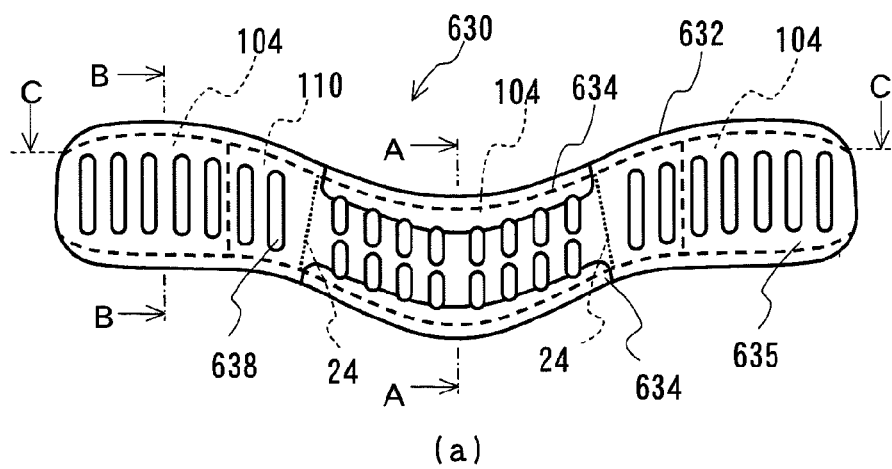
FIG. 20 illustrate a folding cervical vertebra protective band according to an eighth embodiment of the present invention.
Figure 20:
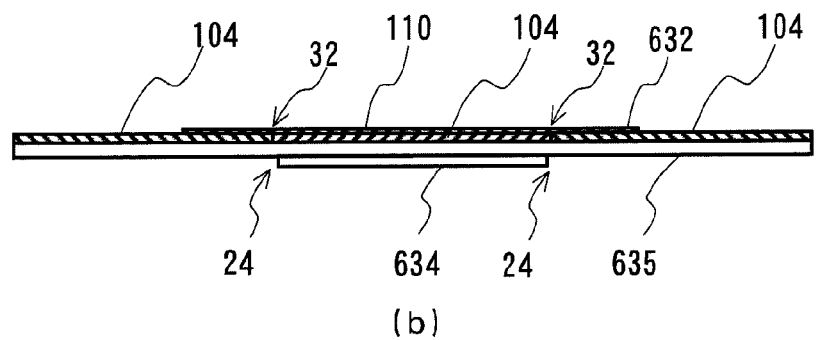
Figure 20:
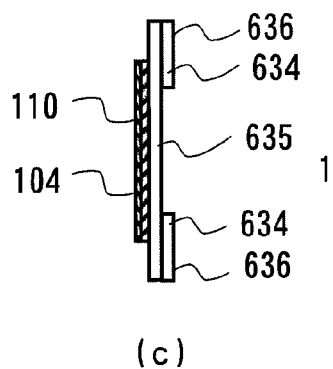
Figure 20:
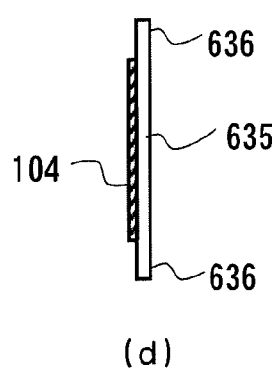
Figure 20:
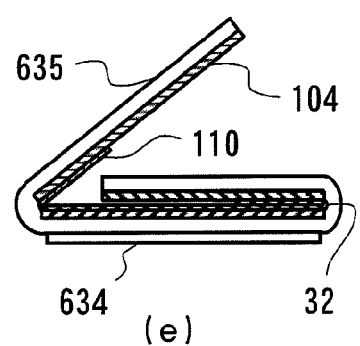

FIG. 20 illustrate a folding cervical vertebra protective band 630 according to this embodiment. The folding cervical vertebra protective band 630 according to this embodiment is an example illustrating a protective band body 632 dedicated for being folded in three. FIG. 20(a) is a front view illustrating a developed state of the folding cervical vertebra protective band 630. FIG. 20(b) is a sectional view taken along the line C-C of FIG. 20(a), which follows a curve (upper dashed line) along the upper edge of the main body layers 104. FIG. 20(c) is a sectional view taken along the line A-A of FIG. 20(a). FIG. 20(d) is a sectional view taken along the line B-B of FIG. 20(a). FIG. 20(e) is a sectional view illustrating, similarly to FIG. 20(b), a folded state in which the folding cervical vertebra protective band 630 is folded in three. Unlike the protective band body 102 of the folding cervical vertebra protective band 100, the protective band body 632 of the folding cervical vertebra protective band 630 is formed as a laminated body including the multiple main body layers 104 which form the triple-divided components dedicated for being folded in three, and the hinge layer 110 for coupling the multiple main body layers 104 to each other. The opposite edge portions 30, which are opposite to each other, of the main body layers 104 adjacent to each other through an intermediation of the hinge portions 24 formed in the protective band body 632, and the hinge layer 110 which is positioned between the opposite edge portions 30 so as to form the bending portions 32 are positioned on the outer surface side in the thickness direction of the protective band body 632.

Note that, in the protective band body 632 formed as the laminated body which includes the multiple main body layers 104 and the hinge layer 110 for coupling the main body layers 104 to each other, the hinge layer 110 is not bonded over the entire surface of the main body layers 104, and arranged at the center of the protective band body 632 while having a length approximately a half of the entire length of the protective band body 632 so as to be bonded to one surface thereof while having the minimum length for coupling the multiple main body layers 104 to each other. With this structure, the hinge portions 24 are formed. In addition, the vicinity of the center is formed as a laminated body, and hence, when compared with the main body layers 104 respectively positioned on the left and right side of the protective band body 632, the central one of the divided components 104 gains enhanced compressive resistance strength in the width direction thereof. As a result, the strength of the protective band body 632 at the portion thereof near the lower jaw portion can be secured.

Further, unlike the protective band body 102 of the folding cervical vertebra protective band 100, the protective band body 632 of the folding cervical vertebra protective band 630 is provided with, over the entire surface on the inner surface side and at a part of both the edge portions thereon which are held in contact with the cervical portion when in use, the cushion plates 634 and the cushion plate 635 for preventing both the edges of the protective band body 632 from being held in direct contact with the cervical portion. The cushion plate 635 is provided over the entire surface of the protective band body 632. Further, the cushion plates 634 are provided separately from each other in the width direction of the protective band body 632 so as to be bonded to the cushion plate 635 in a state of the belt-like shape from thereabove and provided only at the center thereof while having the length substantially one third of the entire length of the protective band body 632. Still further, the cushion plates 634 and 635 have protruding ends 636 which respectively constitute both the upper and lower edge portions protruding outward from both the edges of the protective body band 632. When in use, the protruding ends 636 are deformed in conformity with the shape of the contact position with the cervical portion so as to cover both the edges of the protective band body 632. In this case, the cushion plates 634 and the cushion plate 635 may be reversed in the positional relationship in the thickness direction thereof such that the cushion plates 634 are provided between the central one of the main body layers 104 and the cushion plate 635. The folding cervical vertebra protective band 630 according to this embodiment is designed to enhance the cushioning effect near the lower jaw portion to which especially large load is applied, and to reduce as much as possible the thickness in being folded.

Note that, while the cushion plate 635 is bonded over the entire surface of the protective band body 632 by adhesive, the hinge portions 24 provided at the two position have the portions which extend over the entire region of the hinge portions 24 while having the width of substantially 10 mm (preferably 5 to 20 mm) and to which the cushion plate 635 is not bonded. This is because, when the folding cervical vertebra protective band 630 is folded, with the inner surface side in the thickness direction of the protective band body 632 being on the outer side, the extendable portion of the cushion plate 635 is enlarged. The cushion plate 635 becomes extendable in the range free from being bonded and restricted, whereby the durability against repetitive folding is enhanced.

Further, unlike the protective band body 102 of the folding cervical vertebra protective band 100, the protective band body 632 of the folding cervical vertebra protective band 630 is provided with opening portions 638 which are formed over the entire surface of the region except the hinge portions 24 of the protective band body 632 and which pass through the front and rear surfaces of the protective band body 632. In addition, the opening portions 638 are formed as multiple ovals which pass through both the cushion plates 634 and 635. In a part of the main body layers 104 constituting the central one of the triple-divided components (center which has substantially one third length of that of the protective band body 632), pairs of opening portions are formed in a vertical manner over the width direction. Further, in the other parts of the main body layers 104 constituting the left and right triple-divided components (left and right parts except the center, each of which has substantially the one third length), an opening portion having a shape of a single lengthy hole is formed while extending in a vertical manner over the width direction. Further, the opening portion having the shape of a single lengthy hole and arranged or extending in a vertical manner includes the opening portions 638 arranged in multiple lines over the longitudinal direction of the protective band body 632.

Note that, in the protective band body 632 provided with the opening portions 638, multiple longitudinal ribs with which the upper and lower edge portions are coupled to each other in the width direction are formed while being remained. Therefore, the reduction of the compressive resistance strength of the protective band body 632 is suppressed, whereby large opening portions are formed so as to suitably perform the ventilation between the cervical portion and the outside when in use. Further, the opening portions 638 formed in the left and right triple-divided components 104 of the protective band body 632 and each having the lengthy hole shape are largely opened in the width direction. Thus, when the folding cervical vertebra protective band 630 is curved around the cervical portion, the lateral ends of the protective band body 632 are easily bent in the longitudinal direction, to thereby facilitate the attachment thereof.

Further, unlike the protective band body 102 of the folding cervical vertebra protective band 100, the protective band body 632 of the folding cervical vertebra protective band 630 is not provided with the protruding portion 18 of the protective band body 102 and the attachable/detachable hook/loop fasteners 14 and 16 for holding, when in use, the protective band body 102 in the use state in which the protective band body 102 is curved around the cervical portion. Therefore, it is preferable that the protective band body 632 be covered with a protective cover having both end portions to which paired attachable/detachable holding means for holding the protective band body 632 in the use state are attached, respectively. Alternatively, the protective band body 632 can be covered with the protective cover to which one of the paired attachable/detachable holding means is attached and the other is attached to one end of the protective band body 632 in an attachable/detachable manner. In this case, in this embodiment, for example, one of the attachable/detachable holding means such as paired hook/loop fasteners or paired rubber bands can be attached to one of two of the opening portions 638 each having the shape of the single lengthy hole and respectively positioned on the outermost ends in the longitudinal direction of the protective band body 632.

Figure 21:
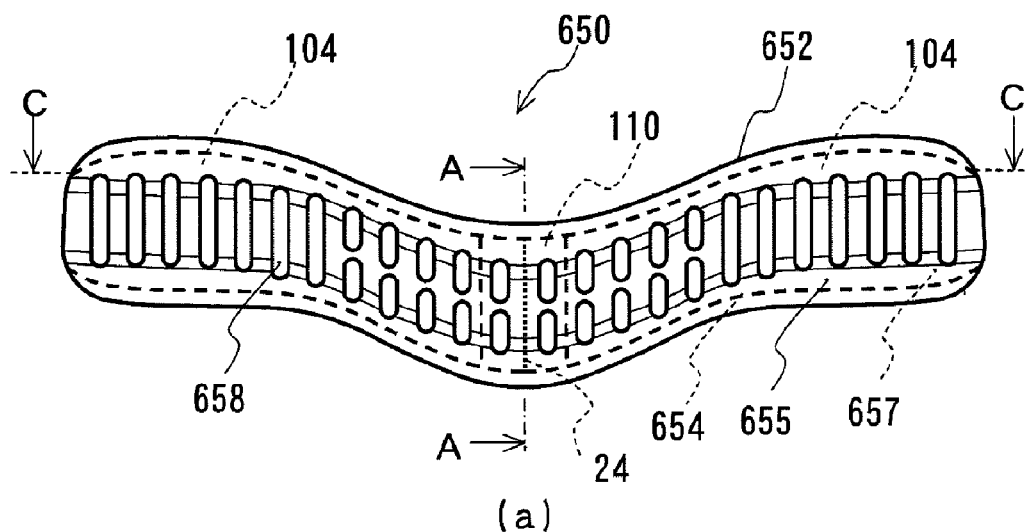
FIG. 21 illustrate a modification of the folding cervical vertebra protective band according to the eighth embodiment of the present invention.
Figure 21:
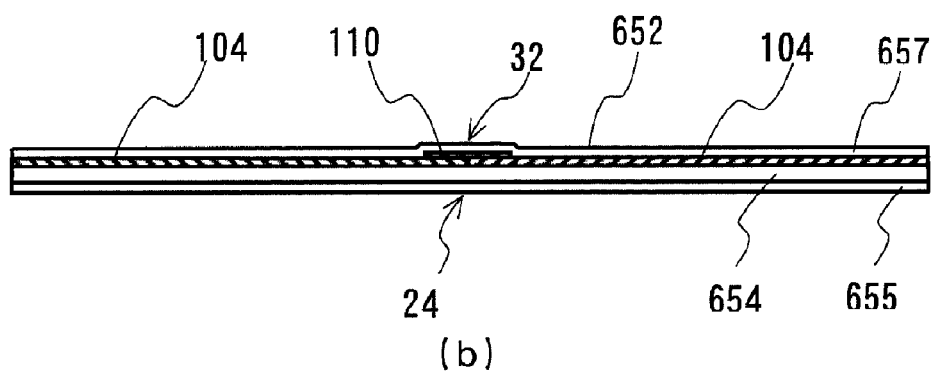
Figure 21:
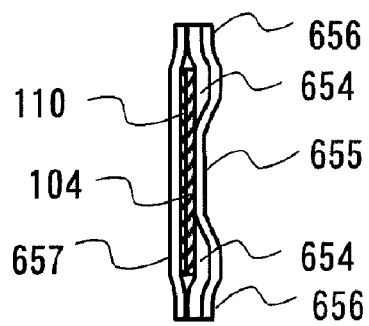
Figure 21:
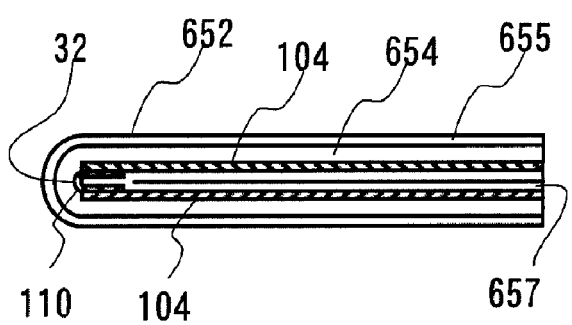

FIG. 21 illustrate a modification of the folding cervical vertebra protective band 630 according to this embodiment. This modification is an example illustrating a cervical vertebra protective band 650 dedicated for being folded in two. FIG. 21(a) is a front view illustrating a developed state of the folding cervical vertebra protective band 650. FIG. 21(b) is a sectional view taken along the line C-C of FIG. 21(a), which follows a curve (upper dashed line) along the upper edge of the main body layers 104. FIG. 21(c) is a sectional view taken along the line A-A of FIG. 21(a). FIG. 21(d) is a sectional view illustrating, similarly to FIG. 21(b), a folded state in which the folding cervical vertebra protective band 650 is folded in two.

Unlike the protective band body 102 of the folding cervical vertebra protective band 100, a protective band body 652 of the folding cervical vertebra protective band 650 is formed as a laminated body including the multiple main body layers 104 which form the dual-divided components dedicated for being folded in two, and the hinge layer 110 for coupling the multiple main body layers 104 to each other. The opposite edge portions 30, which are opposite to each other, of the main body layers 104 adjacent to each other through an intermediation of the hinge portion 24 positioned and formed at the center of the protective band body 652, and the hinge layer 110 which has a predetermined width and is positioned between the opposite edge portions 30 so as to form the bending portion 32 are positioned on the outer surface side in the thickness direction of the protective band body 652. Further, the opening portions 658 are formed over the entire surface of the region except the hinge portion of the protective band body 652, which pass through the front and rear surfaces of the protective band body 652.

Note that, in the protective band body 652 formed as the laminated body which includes the two main body layers 104 and the hinge layer 110 for coupling the two main body layers 104 to each other, the hinge layer 110 is arranged at the center of the protective band body 652 while having a length of approximately 5 cm so as to be bonded thereto while having the minimum length for coupling the two main body layers 104 to each other. With this structure, the hinge portion 24 is formed. As in this embodiment, the hinge layer 110 may be divided only at the portion of the hinge portion, extend to the other portions in which the hinge portion is not formed, be provided between the hinge portions, or may be provided over the entire surface of the protective band body. It suffices that the hinge layer 110 is laminated while having a length equal to or larger than 5 mm or equal to or larger than 1 cm, which is necessary to constitute the bending portion of at least the one hinge portion.

Note that, unlike the protective band body 102 of the folding cervical vertebra protective band 100, the protective band body 652 of the folding cervical vertebra protective band 650 is provided with, over the entire surface on the inner surface side and at both the edge portions thereon which are held in contact with the cervical portion when in use, the cushion plates 654, 655, and 657 for preventing both the edges of the protective band body 652 from being held in direct contact with the cervical portion. Further, the cushion plates 654 and 655 have protruding ends 656 which respectively constitute both the edge portions protruding outward from both the edges of the protective band body 652. When in use, the protruding ends 656 are deformed in conformity with the shape of the contact position with the cervical portion so as to cover both the edges of the protective band body 652.

In this case, the cushion plates 654 each having a relatively large thickness are bonded to both the edge portions of the protective band body 652 while being vertically dual-divided in the width direction so as to be separated from each other. Further, the cushion plate 655 having a relatively small thickness is bonded on the surfaces of the cushion plates 654, in the state in which the cushion plates 654 are bonded thereto, so as to be bonded over the entire surface on the inner surface side of the protective band body 652. Note that, a belt-like recessed portion formed by the cushion plates 654 in the center of the protective band body 652 over the longitudinal direction thereof serves as an inner surface vent path between the cervical portion and the protective band body 652 when in use. Further, the cushion plate 657 is provided over the entire surface on the outer surface side (rear surface side) of the protective band body 652. Therefore, the cushioning performance at the upper and lower edge portions of the protective band body 652 is further enhanced, and the entire of the protective band body 652 is wrapped with the cushion plates. As a result, the soft feel is provided over the entire of the folding cervical vertebra protective band 650.

[Ninth Embodiment]

Next, a ninth embodiment of the folding cervical vertebra protective band of the present invention is described. Note that, in this embodiment, the same constructions as those illustrated in the first and second embodiments are described while denoted by the same reference numerals, and description thereof is omitted.

Figure 22:
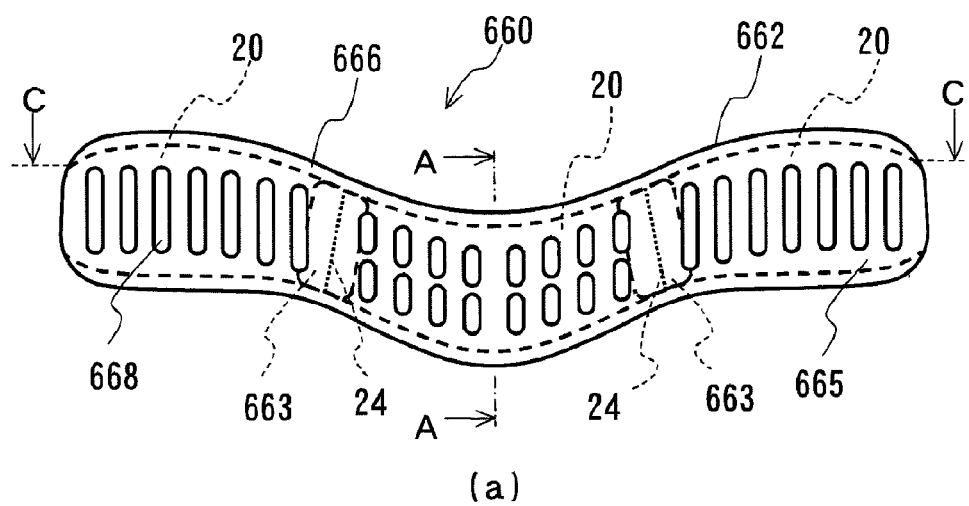
FIG. 22 illustrate a folding cervical vertebra protective band according to a ninth embodiment of the present invention.
Figure 22:
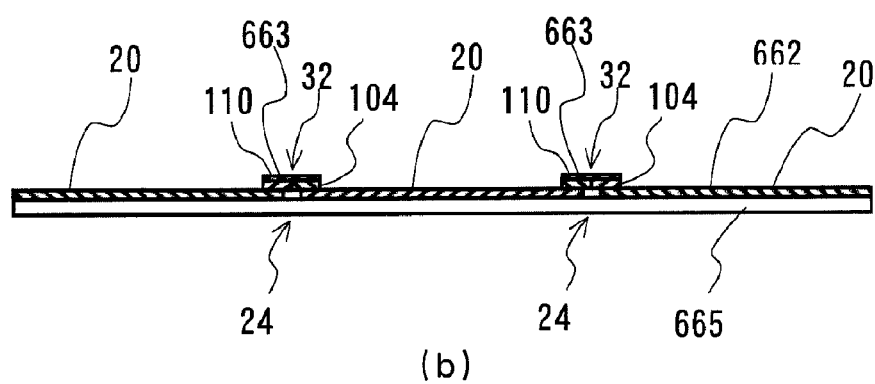
Figure 22:
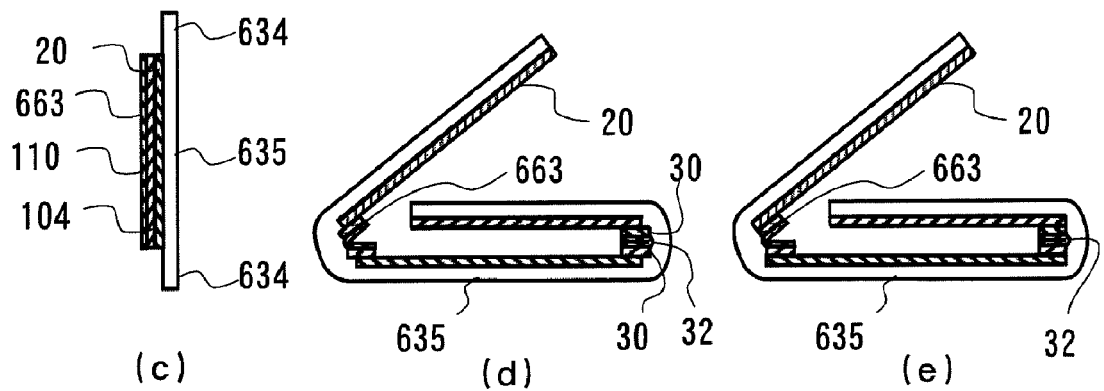

FIG. 22 illustrate a folding cervical vertebra protective band 660 according to this embodiment. FIG. 22(a) is a front view illustrating a developed state of the folding cervical vertebra protective band 660. FIG. 22(b) is a sectional view taken along the line C-C of FIG. 22(a), which follows a curve (upper dashed line) along the upper edge of a protective band body 662. FIG. 22(c) is a sectional view taken along the line A-A of FIG. 22(a). FIG. 22(d) is a sectional view illustrating similarly to FIG. 22(b) how the folding cervical vertebra protective band 660 is folded in three. Further, FIG. 22(e) is a partially sectional explanatory view illustrating a modification of an attachment state between the triple-divided components 20 of the protective band body 662 and hinges 663 constituting the bending portions 32.

Unlike the protective band body 12 of the folding cervical vertebra protective band 10, the protective band body 662 of the folding cervical vertebra protective band 660 is constituted by the three triple-divided components 20 which are dedicated for being folded in three and separated from each other, and the hinge portions 24 are constituted by the sheet-like hinges 663 between the triple-divided components 20 separated from and adjacent to each other. The sheet-like hinges 663 are provided with the opposite edge portions 30 opposite to each other and the bending portions 32 formed between the opposite edge portions (refer to FIG. 22(d)). Those two hinges 663 are attached between the triple-divided components 20 while being bonded thereto so that the protective band body 662 can be folded in three. Further, the protective band body 662 is provided with a cushion plate 665 over the entire surface on the inner side thereof which is held in contact with the cervical portion when in use. The cushion plate 665 has protruding ends 666 which respectively constitute both upper and lower edge portions protruding outward from both the edges of the protective band body 662. Still further, opening portions 668 are formed in a large area in the region except the hinge portions of the protective band body 662, which pass through the front and rear surfaces of the protective band body 662.

Note that, the sheet-like hinges 663 are manufactured, at the manufacturing thereof, integrally with the sheet material constituting the protective band body 102 of the folding cervical vertebra protective band 100 so as to be cut out together with the protective band body 102 from the sheet material. The sheet-like hinges 663 are formed by cutting the peripheries of the portions of the protective band body 662, which correspond to the hinge portions 24 and serve as the substantial centers, to an appropriate size such that the portions thereof, which correspond to the hinge portions 24, constitute the bending portions 32 of the hinges 663. Accordingly, the sheet-like hinges 663 is formed as a laminated body including the main body layers 104 and the hinge layers 110 for coupling the main body layers 104 which are obtained as a result of a dual separation. The opposite edge portions 30, which are opposite to each other, of the main body layers 104 adjacent to each other through an intermediation of the hinges 663 forming the hinge portions 24 of the protective band body 662, and the hinge layers 110 each of which is positioned between the opposite edge portions 30 so as to form the bending portions 32 are positioned on the outer surface side in the thickness direction of the hinges 663. With this structure, the thickness of the protective band body 662 of the folding cervical vertebra protective band 660 can be reduced in being folded. The sheet-like hinges 663 as described above, similarly to the protective band body 662, are manufactured as a laminated body formed of a plastic material, a rubber material, a metal material, or a material obtained by combining two or more of those materials selected therefrom.

In this context, how to attach the sheet-like hinges 663 and the protective band body 662 to each other is described. For example, as illustrated in FIGS. 22(*b*) and (*d*), in order that the edge portions, which are opposite to each other, of the triple-divided components 20 of the protective band body 662 are not collided against each other while maintaining predetermined gaps therebetween when in use, only the opposite edge portions 30, which are opposite to each other, of the sheet-like hinges 663 may be collided against each other in a butting manner. Alternatively, as illustrated in FIG. 22(*e*) described above, the edge portions, which are opposite to each other, of the triple-divided components 20 constitute the opposite edge portions so as to be collided against the opposite edge portions 30, which are opposite to each other, of the sheet-like hinges 663 in a butting manner, whereby the colliding area of the opposite surfaces may be increased.

Figure 23:
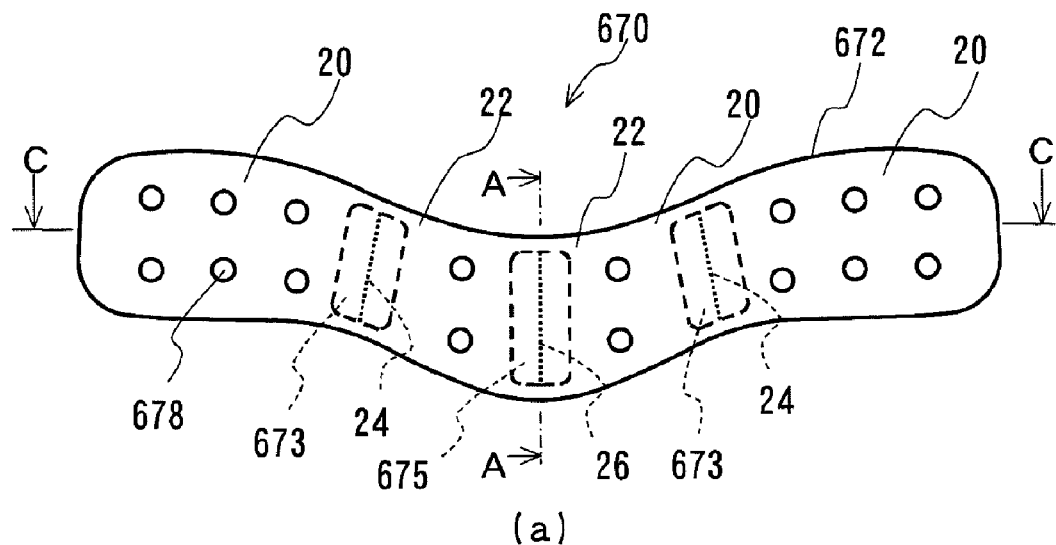
FIG. 23 illustrate a modification of the folding cervical vertebra protective band according to the ninth embodiment of the present invention.
Figure 23:
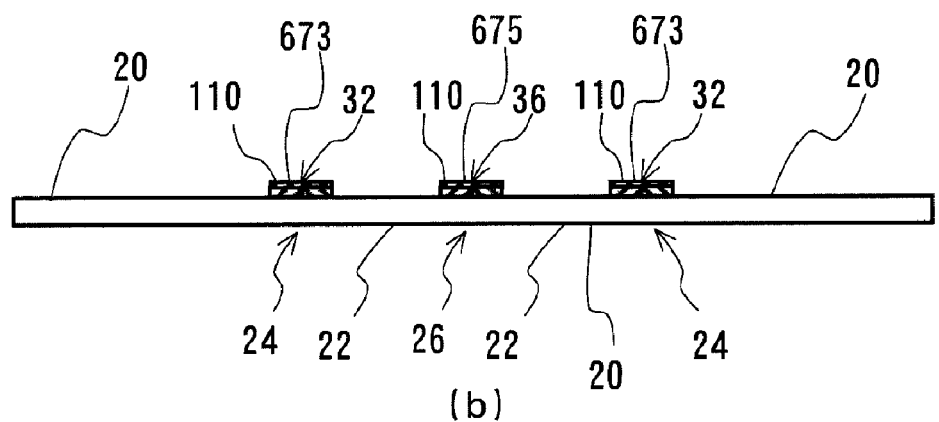
Figure 23:
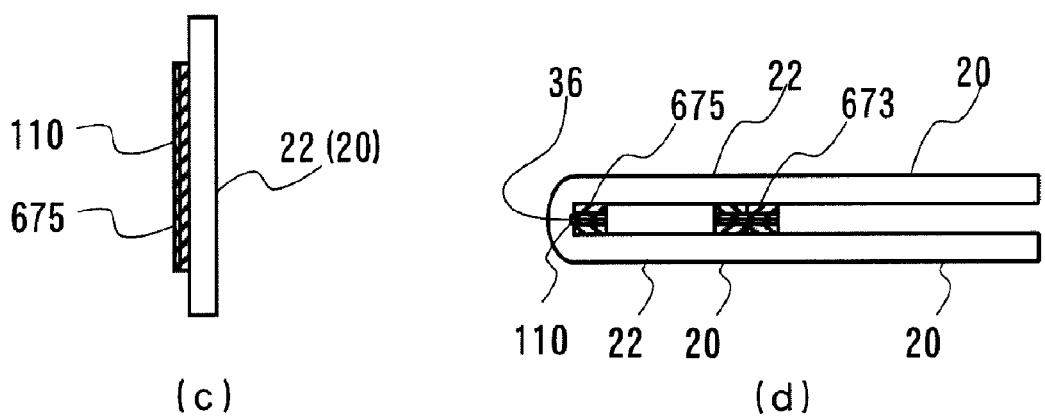

FIG. 23 illustrate a modification of the folding cervical vertebra protective band 660 according to this embodiment. This modification is an example illustrating a folding cervical vertebra protective band 670. FIG. 23(*a*) is a front view illustrating a developed state of the folding cervical vertebra protective band 670. FIG. 23(*b*) is a sectional view taken along the line C-C which passes the center in the width direction of FIG. 23(*a*). FIG. 23(*c*) is a sectional view taken along the line A-A of FIG. 23(*a*). FIG. 23(*d*) is a sectional view illustrating similarly to FIG. 23(*b*) a folded state in which the folding cervical vertebra protective band 670 is folded in two. Unlike the protective band body 12 of the folding cervical vertebra protective band 10, the protective band body 672 of the folding cervical vertebra protective band 670, which are constituted by the triple-divided components 20, is formed of a relatively flexible synthetic resin foam. The hinge portions 24 are constituted by sheet-like hinges 673 which are attached between the triple-divided components 20 adjacent to each other. The sheet-like hinges 673 are provided with the opposite edge portions 30 opposite to each other and the bending portions 32 formed between the opposite edge portions. The hinge portion 26 is constituted by a sheet-like hinge 675 which are attached between the subdivided components 22 adjacent to each other. The hinge 675 is provided with the opposite edge portions 34 opposite to each other and the bending portion 36 between the opposite edge portions. The hinges 673 and the hinge 675 are attached while being bonded between the triple-divided components 20 and the subdivided components 22, respectively. Further, opening portions 678, which pass through the front and rear surfaces of the protective band body 672, are formed over the entire surface of the region except the hinge portions of the protective band body 672.

Note that, the hinges 673 and the hinge 675 are sheet-like hinges formed similarly to the sheet-like hinges 663 which are adopted for the protective band body 662 of the folding cervical vertebra protective band 660. Accordingly, those sheet-like hinges 673 and hinge 675 are formed as a laminated body including the main body layers 104 (106) and the hinge layers 110 for coupling the main body layers 104 (106) which are separated from each other. The following are positioned on the outer surface side in the thickness direction of the hinges 673 and the hinge 675: the opposite edge portions 30, which are opposite to each other, of the main body layers 104 adjacent to each other through an intermediation of the hinges 673 constituting the hinge portions 24, and the hinge layers 110 which are positioned between the opposite edge portions 30 so as to form the bending portions 32; and the opposite edge portions 34, which are opposite to each other, of the main body layers 106 adjacent to each other through an intermediation of the hinge 675 constituting the hinge portion 26, and the hinge layer 110 which is positioned between the opposite edge portions 34 so as to form the bending portion 36.

Further, unlike the protective band body 662 of the folding cervical vertebra protective band 660, in the protective band body 672 of the folding cervical vertebra protective band 670, the divided components 20 and 22 are not separated from each other at the hinge portions 24 and 26, respectively, and the divided components 20 of the protective band body 672 are integrally formed. Note that, when the folding cervical vertebra protective band 670 is folded, the protective band body 672 formed of a relatively flexible synthetic resin foam extends to be deformed at the bending portions 32 and 36, thereby being folded at the hinge portions 24 and 26 of the hinges 673 and 675, respectively. In addition, the hinges 673 and 675 constituting the hinge portions 24 and 26 are attached to the protective band body 672 while being retracted inward with respect to both the edges thereof, and are arranged so as to prevent direct contact with the cervical portion when in use. Note that, in the protective band body 672 of the folding cervical vertebra protective band 670, the process traces corresponding to the hinge portions 24 and 26 of the protective band body 12 of the folding cervical vertebra protective band 10 may be formed, or the divided components 20 (22) may be separated from each other.

Figure 24:
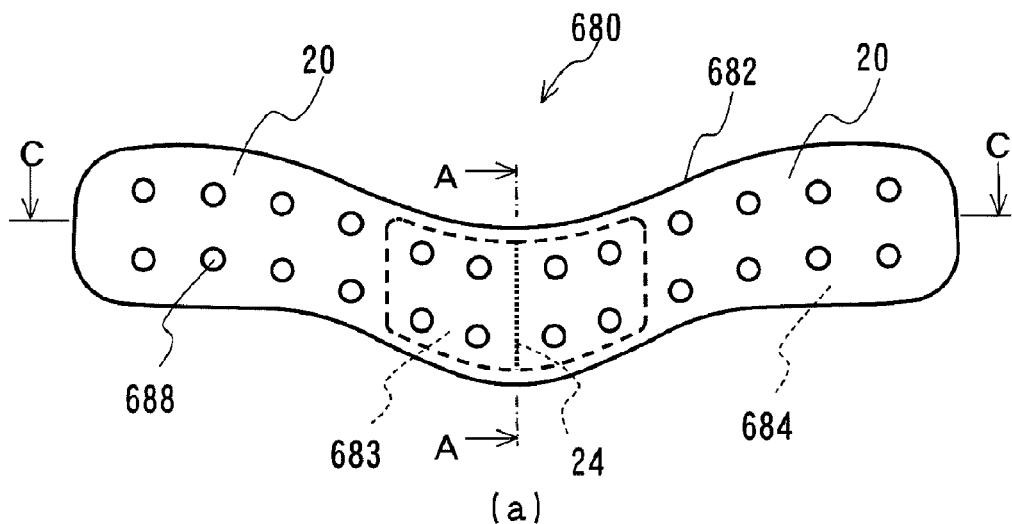
FIG. 24 illustrate another modification of the folding cervical vertebra protective band according to the ninth embodiment of the present invention.
Figure 24:
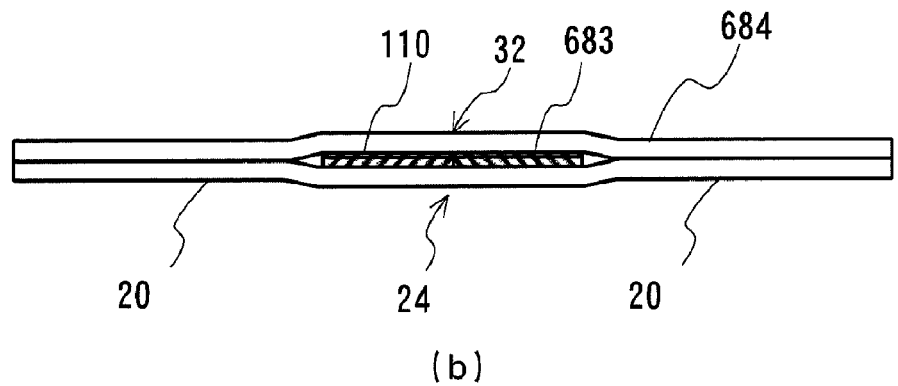
Figure 24:
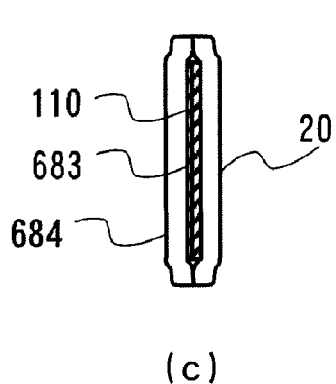
Figure 24:
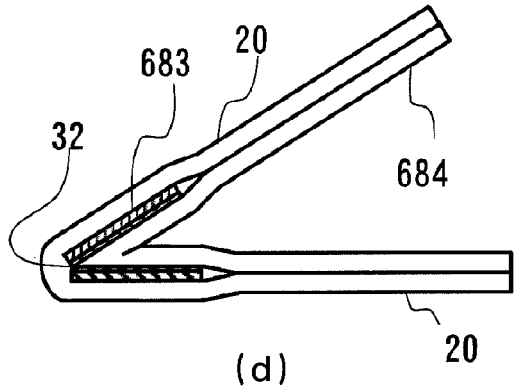

FIG. 24 illustrate a modification of the folding cervical vertebra protective band 670 according to this embodiment. This modification is an example illustrating a folding cervical vertebra protective band 680 dedicated for being folded in two. FIG. 24(*a*) is a front view illustrating a developed state of the folding cervical vertebra protective band 680. FIG. 24(*b*) is a sectional view taken along the line C-C which passes the substantial center in the width direction of FIG. 24(*a*). FIG. 24(*c*) is a sectional view taken along the line A-A of FIG. 24(*a*). FIG. 24(*d*) is a sectional view illustrating similarly to FIG. 24(b) how the folding cervical vertebra protective band 680 is folded in two. Unlike the protective band body 672 of the folding cervical vertebra protective band 670, in the protective band body 682 of the folding cervical vertebra protective band 680, the two divided components 20 dedicated for being folded in two are formed of a relatively flexible synthetic resin foam. The hinge portion 24 is constituted by a sheet-like hinge 683 which is attached between the divided components 20 adjacent to each other. The hinge 683 is provided with the opposite edge portions 30 opposite to each other and the bending portion 32 formed between the opposite edge portions. The sheet-like hinge 683, which is constituted similarly to the hinges 673 and 675 of the protective band body 672 of the folding cervical vertebra protective band 670, is attached while being bonded between the two divided components 20. The hinge layer 110 forming the bending portion 32 is positioned on the outer surface side in the thickness direction of the hinge 683. In addition, a cushion plate 684 having the same shape as that of the protective band body 682 is provided over the entire surface on the outer surface side of the protective band body 682. Further, opening portions 688 are formed over the entire surface of the region except the hinge portion of the protective band body 682, which pass through the front and rear surfaces of the protective band body 682.

Note that, the sheet-like hinge 683 has the hinge portion 24 which is provided at substantially the center thereof and extends in the width direction, has substantially one third length of that of the protective band body 682, and is attached while being bonded to substantially the center of the protective band body 682. Thus, the compressive resistance strength in the width direction of the protective band body 682, which is formed of a relatively flexible synthetic resin foam, is increased at the center thereof owing to the presence of the sheet-like hinge 683, whereby the strength of the protective band body 682 at the portion thereof near the lower jaw portion is increased. Further, the cushion plate 684 is bonded over the entire surface on the outer surface side in the thickness direction of the protective band body 682. Therefore, in a mode, the entire of the protective band body 682 is covered with the synthetic resin foam and the cushion plate 684 around the sheet-like hinge 683 which is formed to be relatively large, whereby the hinge 683 is prevented from being held in direct contact with the cervical portion when in use.

Note that, when the folding cervical vertebra protective band 680 is folded, the protective band body 682 which is formed of a relatively flexible synthetic resin foam extends to be deformed at the bending portion 32, and the cushion plate 684 is compressed to be deformed so that the protective band body 682 can be folded at the hinge portion 24 of the hinge 683. Note that, in the protective band body 682 of the folding cervical vertebra protective band 680, the process traces corresponding to the hinge portions 24 of the protective band body 12 of the folding cervical vertebra protective band 10 may be formed, or the divided components 20 may be separated from each other.

[Tenth Embodiment]

Next, a tenth embodiment of the folding cervical vertebra protective band of the present invention is described. Note that, in this embodiment, the same constructions as those illustrated in the first embodiment are described while denoted by the same reference numerals, and description thereof is omitted.

Figure 25:
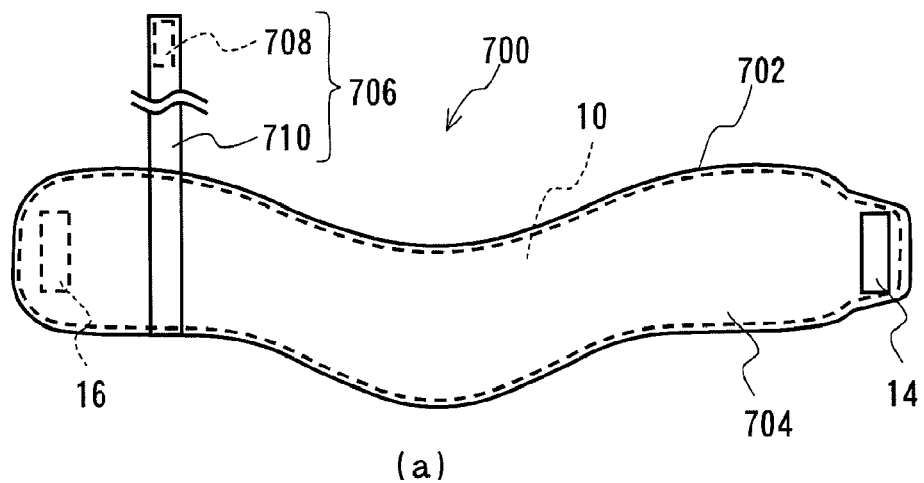
FIG. 25 illustrate a folding cervical vertebra protective band according to a tenth embodiment of the present invention.
Figure 25:
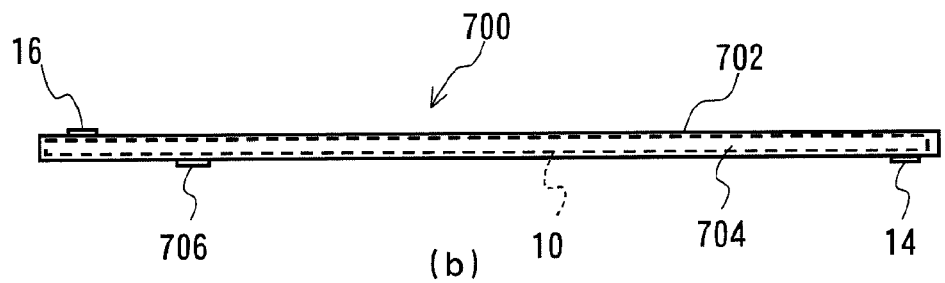
Figure 25:
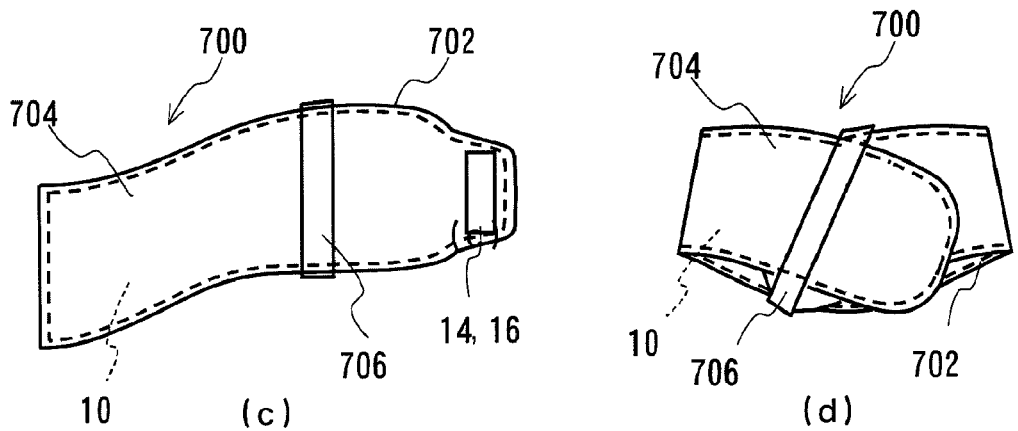

FIG. 25 illustrate a folding cervical vertebra protective band 700 according to this embodiment. FIG. 25(a) is a front view illustrating a developed state of the folding cervical vertebra protective band 700. FIG. 25(b) is a top view illustrating a developed state of the folding cervical vertebra protective band 700. FIG. 25(c) is a front view illustrating a folded state in which the folding cervical vertebra protective band 700 is folded in two. FIG. 25(d) is a front view illustrating a folded state in which the folding cervical vertebra protective band 700 is folded in three. Unlike the protective band body 12 of the folding cervical vertebra protective band 10, a protective band body 702 of the folding cervical vertebra protective band 700 is covered with a protective cover 704 which is wholly flexible and detachable. The protective cover 704 is provided with a holding means 706 for holding the folded protective band body 702 in a folded state. The holding means 706 is constituted by a hook/loop fastener 708 and a belt-like hook/loop fastner 710. When the protective band body 702 is folded, the belt-like hook/loop fastener 710 is wound such that the hook/loop fastener 708 is fixed thereto, whereby the folded protective band body 702 can be held in a folded state.

Note that, unlike the protective band body 12 of the folding cervical vertebra protective band 10, in the protective band body 702 of the folding cervical vertebra protective band 700, the hook/loop fasteners 14 and 16 are attached to both the edge portions of the protective cover 704, respectively. The hook/loop fasteners 14 and 16 provided to the folding cervical vertebra protective band 10 can be omitted and serve as an attachable/detachable holding means for holding the protective band body 702 in a use state of being curved around the cervical portion. Note that, it is possible to attach one of the hook/loop fasteners 14 and 16 to one end of the protective band body 12 of the folding cervical vertebra protective band 10, and possible to attach the other to one end of the protective cover 704. Alternatively, it is also possible to omit the hook/loop fasteners 14 and 16 of the protective cover 704 so as to construct the protective cover 704 having a shape in which both the ends thereof are opened. In this case, the hook/loop fasteners 14 and 16 of the protective band body 12 of the folding cervical vertebra protective band 10 serve as the attachable/detachable holding means for holding the protective band body 702 in a use state.

Note that, it is preferable that the protective cover 704 be manufactured, when taking direct contact along the cervical portion of the user into consideration, with use of a wholly flexible material including woven cloth made of natural fiber or synthetic fiber and knitted cloth, and have the structure in which the protective band body 12 of the folding cervical vertebra protective band 10 is detachable. The protective cover 704 of this embodiment is manufactured through sewing process of the polyester-fiber woven cloth so as to be detachable by opening a slide fastener (not shown) linearly provided in the rear surface (surface exposed to the outer side when in use) in the longitudinal direction of the protective cover 704. With this structure, the protective cover 704 can be easily detached from the protective band body 12 so as to be washed, and hence a hygienic condition can be maintained for a long period of time. Further, the cushion plate can be arranged on the inside of the protective cover so as to increase the wearing comfort.

Figure 26:
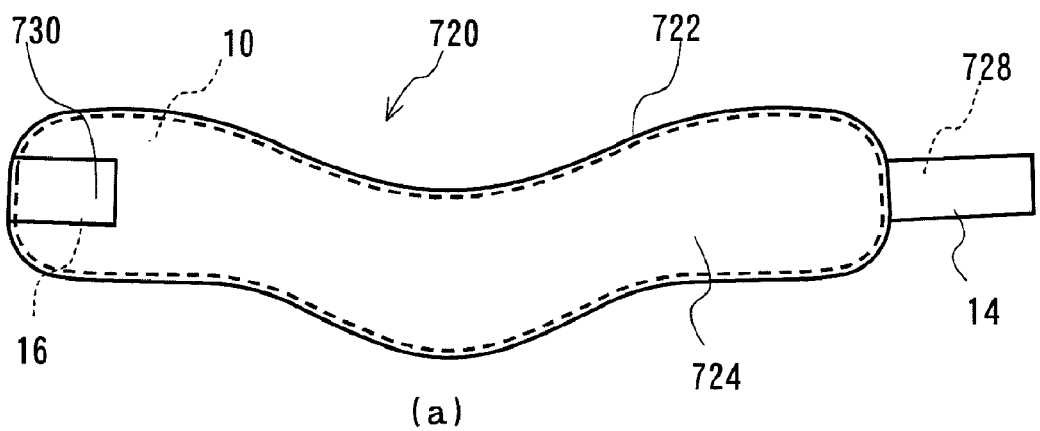
FIG. 26 illustrate a modification of the folding cervical vertebra protective band according to the tenth embodiment of the present invention.
Figure 26:
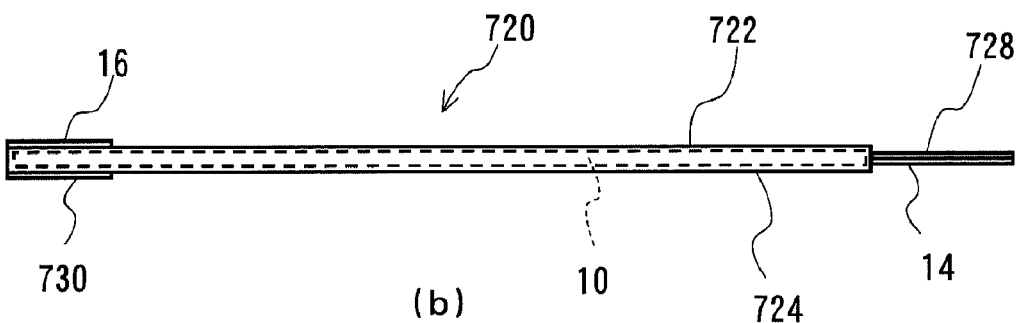
Figure 26:
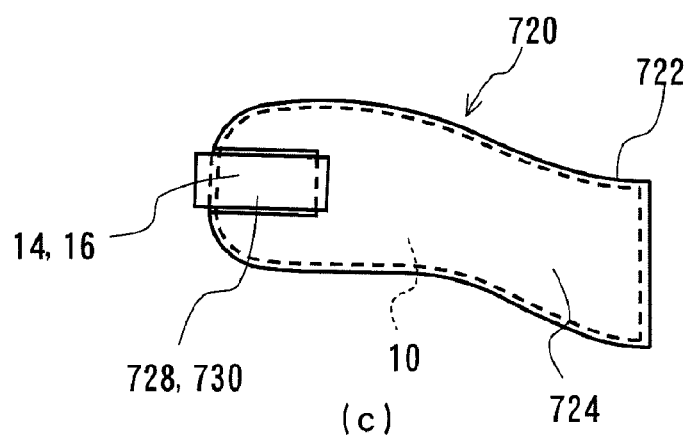

FIG. 26 illustrate a modification of the folding cervical vertebra protective band 700 according to this embodiment. FIG. 26(a) is a developed view illustrating a developed state of a folding cervical vertebra protective band 720 which is a modification of the folding cervical vertebra protective band 700. FIG. 26(b) is a top view illustrating the developed state of the folding cervical vertebra protective band 720. FIG. 26(c) is a front view illustrating a folded state in which the folding cervical vertebra protective band 720 is folded in two. The protective band body 722 of the folding cervical vertebra protective band 720 is covered with the protective cover 724 which is wholly flexible and detachable. The protective cover 724 has at one end thereof the hook/loop fastener 14 formed in a belt-like shape and a hook/loop fastener 728 provided on the rear surface of the hook/loop fastener 14. Further, the protective cover 724 has at the other end thereof a hook/loop fastener 730 and the hook/loop fastener 16 provided on the rear surface side of the hook/loop fastener 730. In this case, the hook/loop fasteners 728 and 730 are paired holding means for holding the folded protective band body 722 in a folded state, and further, the hook/loop fasteners 14 and 16 are paired attachable/detachable fixing means for holding the protective band body 722 in a use state.

Note that, unlike the protective band body 12 of the folding cervical vertebra protective band 10, the protective band body 722 of the folding cervical vertebra protective band 720 is not provided with the protruding portion 18 of the protective band body 12. The protruding portion 18 serves as a protruding portion for forming the holding means for holding the protective band body in a use state, and hence the protruding portion 18 can be omitted from the protective band body 722 in which the protective cover 724 is provided with a fixing means. Accordingly, the protective band body 722 can be formed in a symmetrical shape.

Note that, when magnets and the like are embedded with the protective cover, the cushion plate, the protective band body, and the like which constitute the folding cervical vertebra protective band of the present invention, health promoting function such as improvement of the circulation of the blood around the cervical portion and prevention of frozen shoulder can be provided thereto.

As described in the above-mentioned embodiments, the folding cervical vertebra protective band has, for example, high compressive resistance strength sufficient for standing to some extent the large forward pressure applied to the cervical portion in proportion to the weight of the head at the time of a rear-end accident or the like, and has a sufficient cervical vertebra protective function. In addition, the folding cervical vertebra protective band has the divided components obtained as a result of multiple divisions in the longitudinal direction of the protective band body thereof, and has the hinge portions for foldably coupling the multiple divided components to each other therebetween. With this structure, the entire of the folding cervical vertebra protective band is curved around the cervical portion and attached to the cervical portion when in use, and can be folded into a smaller size in two, three, or more at the hinge portions except when in use. As a result, the folding cervical vertebra protective band can be easily accommodated in a handbag or a pocket of a suit, and hence the portability thereof is remarkably increased. As a result, in a preventative view and for the safety, for example, mildly-ill patients or the like can always carry the folding cervical vertebra protective band in a bag, a handbag, a pocket of a suit, or the like when necessary.

Note that, the present invention is not limited to the above-mentioned embodiments. In addition to the modification of combining the above-mentioned embodiments, various modifications can be made thereto without departing from the spirit of the present invention.

The invention claimed is:
1. A folding cervical vertebra protective band, comprising:
a belt-like protective band body which has a length and a width for substantially surrounding an entirety of a cervical portion of a user; and
an attachable/detachable fixing means for holding the protective band body, when in use, around the cervical portion,
wherein the protective band body comprises multiple divided components obtained as a result of multiple divisions of the protective band body in a longitudinal direction thereof and also comprises hinge portions for foldably coupling the multiple divided components to each other, each of the hinge portions having opposite edge portions of the multiple divided components adjacent to each other and bending portions which are positioned between the opposite edge portions and are positioned on an outer surface side when in use and said bending portions extend in a width direction of the protective band body, and
wherein during use the folding cervical vertebra protective band is curved around the cervical portion of the user so as to be attached to the cervical portion without being bent at the bending portions owing to the opposite edge portions of the hinge portions, which are engaged with each other in an abutting manner when in use, and
when not in use, the hinge portions are bent in a direction opposite to a curve direction at the bending portions so as to allow the cervical vertebra protective band to be folded into a smaller size while an inner surface side of the protective band body is exposed to an outer side.

2. A folding cervical vertebra protective band according to claim 1, wherein the protective band body comprises triple-divided components which are obtained as a result of a triple division of an entire of the protective band body so as to have substantially the same lengths.

3. A folding cervical vertebra protective band according to claim 2, wherein a central one of the triple-divided components comprises subdivided components which are obtained as a result of a further dual division of the central one of the triple-divided components so as to have substantially the same lateral lengths.

4. A folding cervical vertebra protective band according to claim 1, wherein the hinge portions comprise the opposite edge portions, which are opposite to each other, of the multiple divided components adjacent to each other, and a hinge which is attached between the opposite edge portions and constitutes one of the bending portions.

5. A folding cervical vertebra protective band according to claim 4, wherein the hinge comprises a sheet-like hinge which comprises a laminated body including a pair of main body layers and a hinge layer for coupling the pair of main body layers to each other and forming the bending portions.

6. A folding cervical vertebra protective band according to claim 1, wherein the protective band body is provided with, over an entire surface and/or at both edge portions on an inner surface side thereof which are held in contact with the cervical portion at least when in use, a cushion plate for preventing both edges of the protective band body from being held in direct contact with the cervical portion.

7. A folding cervical vertebra protective band according to claim 6, wherein the cushion plate has protruding ends which have both edge portions protruding outward from both the edges of the protective band body, the protruding ends being deformed in conformity with a shape of a contact position with the cervical portion so as to cover both the edges of the protective band body when in use.

8. A folding cervical vertebra protective band according to claim 1, wherein the protective band body comprises a pair of dual-divided components which are obtained as a result of a dual division of the protective band body so as to have substantially the same lateral lengths.

9. A folding cervical vertebra protective band according to claim 1, wherein the protective band body comprises the multiple divided components which are obtained as a result of multiple divisions, which are performed four times or more, of the entire of the protective band body so as to have substantially the same lengths.

10. A folding cervical vertebra protective band according to claim 1, wherein
the protective band body is formed of a single plate member, and
the hinge portions are formed of process traces of slitting, notching, machining, or embossing which is effected on a front surface or a rear surface of the plate member which forms the protective band body.

11. A folding cervical vertebra protective band according to claim 1, wherein
the protective band body comprises a laminated body including multiple main body layers which form the multiple divided components and a hinge layer for coupling the multiple main body layers to each other, and
the hinge portions formed in the protective band body comprise:
opposite edge portions, which are opposite to each other, of the main body layers adjacent to each other; and
the hinge layer is positioned between the opposite edge portions so as to form the bending portions.

12. A folding cervical vertebra protective band according to claim 1, wherein the hinge portions comprise a hinge which is attached between the multiple divided components adjacent to each other and forms one of the bending portions, the hinge being provided with the opposite edge portions which are opposite to each other and constitute the hinge portions.

13. A folding cervical vertebra protective band according to claim 1, wherein the opposite edge portions of the multiple divided components or of the main body layers, which form the hinge portions, comprise rib portions having thicknesses larger than thicknesses of general portions of the multiple divided components or of the main body layers.

14. A folding cervical vertebra protective band according to claim 1, wherein
the protective band body is substantially symmetrically with respect to a center in the longitudinal direction thereof, and
the hinge portions for dividing the protective band body into, the multiple divided components are formed such that the multiple divided components are substantially superimposed on each other when the protective band body is folded with use of the hinge portions.

15. A folding cervical vertebra protective band according to claim 1, wherein the multiple divided components of the protective band body comprise divided component bodies serving as a main body thereof and height adjustment members attached to the divided component bodies while being attachable/detachable.

16. A folding cervical vertebra protective band according to claim 1, wherein the protective band body is provided with opening portions which pass through front and rear surfaces of the protective band body, the opening portions being formed in a region except the hinge portions of the protective band body.

17. A folding cervical vertebra protective band according to claim 1, wherein the protective band body is covered with a protective cover, the protective cover being provided with a holding means for holding the folded protective band body in a folded state thereof.

18. A folding cervical vertebra protective band according to claim 1, wherein an attachable/detachable fixing means for holding the protective band body in the use state thereof comprises paired attachable/detachable portions which are attached to both ends of the protective band body, respectively.

19. A folding cervical vertebra protective band according to claim 1, wherein
the protective band body is covered with the protective cover, and
an attachable/detachable fixing means for holding the protective band body in the use state thereof comprises paired attachable/detachable portions which are attached to both ends of the protective cover, respectively.

20. A folding cervical vertebra protective band according to claim 1, wherein
the protective band body is covered with the protective cover, and
an attachable/detachable fixing means for holding the protective band body in the use state thereof comprises paired attachable/detachable portions one of which is attached to one end of the protective band body and another one of which is attached to one end of the protective cover.

21. A folding cervical vertebra protective band, comprising:
a belt-like protective band body which has a length and a width for substantially surrounding an entirety of a cervical portion of a user; and
an attachable/detachable fixing means for holding the protective band body, when in use, around the cervical portion,
wherein the protective band body has multiple divided components obtained as a result of multiple division of the protective band body in a longitudinal direction thereof and also has hinge portions for foldably coupling the multiple divided components to each other, and is attached to the cervical portion when in use, and is folded into a small size with use of the hinge portions when not in use, and wherein
the multiple divided components of the protective band body comprise multiple divided component bodies serving as a main body thereof and height adjustment members attached to the divided component bodies while being attachable/detachable.

* * * * *